US010188515B2

(12) United States Patent
Duffy et al.

(10) Patent No.: US 10,188,515 B2
(45) Date of Patent: Jan. 29, 2019

(54) DEVICES AND METHODS FOR CRIMPING A MEDICAL DEVICE

(71) Applicant: Medtronic Vascular Galway, Ballybrit, Galway (IE)

(72) Inventors: Niall Duffy, Ballybrit (IE); Marian Creaven, Ballybrit (IE); Philip Haarstad, Chanhassen, MN (US); Frank Harewood, Ballybrit (IE); Igor Kovalsky, Minnetonka, MN (US); Jason Quill, Forest Lake, MN (US); Daniel Gelfman, Golden Valley, MN (US); Ana Menk, St. Paul, MN (US); Darren Janzig, Center City, MN (US); Shyam Gokaldas, New Brighton, MN (US); Kenneth Warnock, Manchester, MN (US)

(73) Assignee: MEDTRONIC VASCULAR INC., Santa Rosa, CA (US)

( * ) Notice: Subject to any disclaimer, the term of this patent is extended or adjusted under 35 U.S.C. 154(b) by 1065 days.

(21) Appl. No.: 14/272,717

(22) Filed: May 8, 2014

(65) Prior Publication Data

US 2014/0331475 A1    Nov. 13, 2014

Related U.S. Application Data

(60) Provisional application No. 61/822,601, filed on May 13, 2013.

(51) Int. Cl.
*A61F 2/24* (2006.01)
*B23P 11/00* (2006.01)
(Continued)

(52) U.S. Cl.
CPC ............ *A61F 2/243* (2013.01); *A61F 2/0095* (2013.01); *A61F 2/2436* (2013.01); *A61F 2/95* (2013.01);
(Continued)

(58) Field of Classification Search
CPC ............ A61F 2/2436; A61F 2002/9522; A61F 2/0095; B23P 11/005; B23P 19/04;
(Continued)

(56) References Cited

U.S. PATENT DOCUMENTS 6,090,035 A * 7/2000 Campbell ................. A61F 2/95
600/3
9,649,212 B2 * 5/2017 Fargahi ..................... A61F 2/95
(Continued)

FOREIGN PATENT DOCUMENTS

WO    WO2010/121076    10/2010
WO    WO2012/106491    8/2012

OTHER PUBLICATIONS

PCT/US2014/037567, International Search Report and Written Opinion, dated Aug. 6, 2014.

*Primary Examiner* — Matthew P Travers
(74) *Attorney, Agent, or Firm* — Medler Ferro Woodhouse & Mills PLLC

(57) ABSTRACT

Devices, systems, and methods for crimping a medical device are disclosed. More specifically, the present disclosure relates to devices, systems, and methods for reducing the diameter of a collapsible heart valve prosthesis to be loaded onto a delivery device. The devices, systems, and methods using at least one funnel to crimp the heart valve prosthesis and load it onto the delivery system.

9 Claims, 24 Drawing Sheets

(51) Int. Cl.
*A61F 2/95* (2013.01)
*A61F 2/00* (2006.01)

(52) U.S. Cl.
CPC ..... *B23P 11/005* (2013.01); *A61F 2002/9522* (2013.01); *Y10T 29/49863* (2015.01); *Y10T 29/53987* (2015.01)

(58) Field of Classification Search
CPC ......... Y10T 29/49909; Y10T 29/49913; Y10T 29/53652; Y10T 29/53657; Y10T 29/53952; Y10T 29/53987; Y10T 29/53996
See application file for complete search history.

(56) References Cited

U.S. PATENT DOCUMENTS

| | | |
|---|---|---|
| 2006/0265056 A1 | 11/2006 | Nguyen et al. |
| 2007/0162100 A1* | 7/2007 | Gabbay ............... A61F 2/95 623/1.11 |
| 2007/0239266 A1 | 10/2007 | Birdsall |
| 2007/0239269 A1 | 10/2007 | Dolan et al. |
| 2007/0239271 A1 | 10/2007 | Nguyen |
| 2008/0071362 A1 | 3/2008 | Tuval et al. |
| 2010/0049313 A1 | 2/2010 | Alon et al. |
| 2010/0298931 A1* | 11/2010 | Quadri ............... A61F 2/2418 623/2.11 |
| 2011/0208296 A1 | 8/2011 | Duffy et al. |
| 2011/0295216 A1 | 12/2011 | Miller |
| 2011/0319988 A1* | 12/2011 | Schankereli ........ A61F 2/2418 623/2.11 |
| 2012/0330408 A1* | 12/2012 | Hillukka ............ A61F 2/0095 623/2.11 |
| 2014/0155990 A1* | 6/2014 | Nyuli ............... A61F 2/2418 623/2.11 |
| 2014/0222142 A1 | 8/2014 | Kovalsky et al. |

* cited by examiner

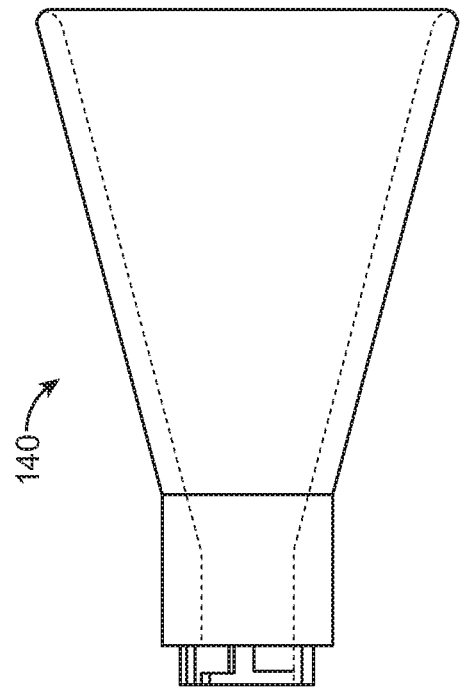
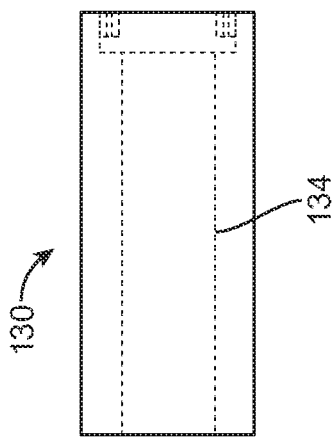
FIG. 4

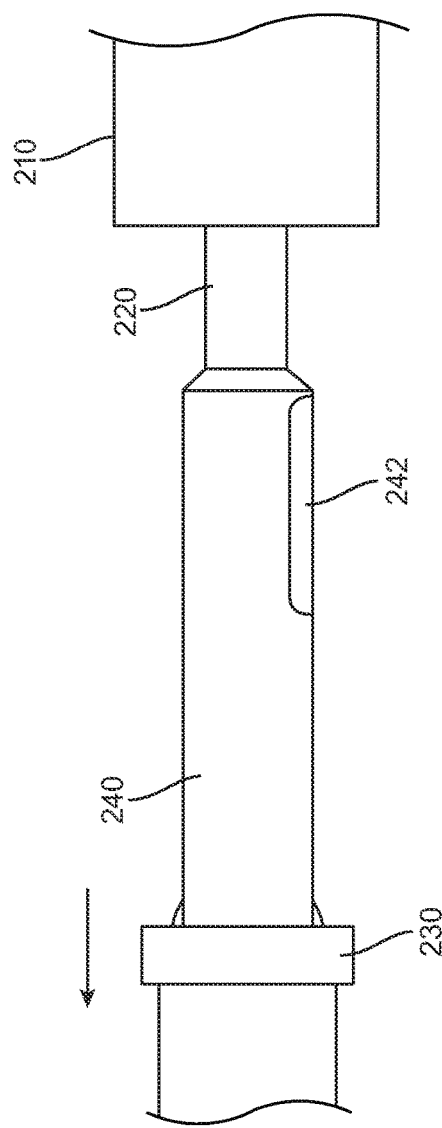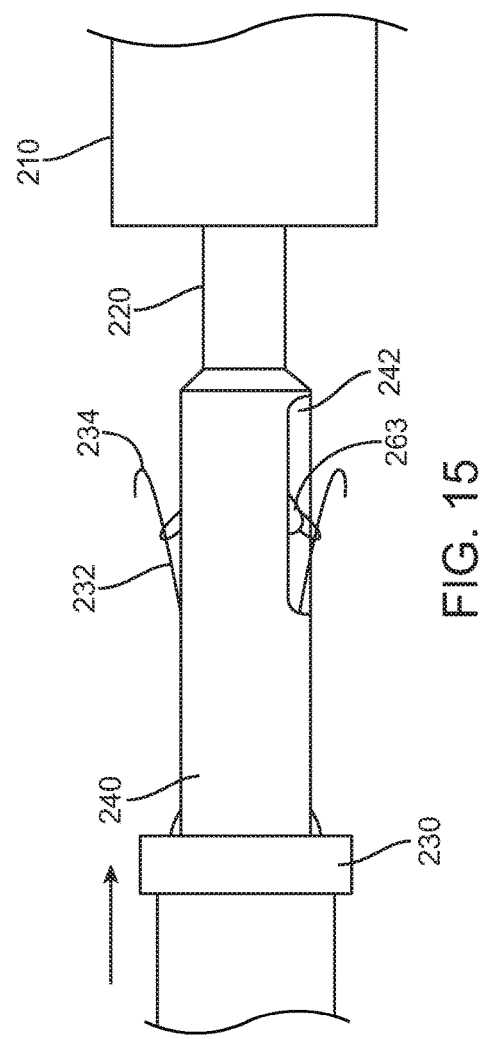

DEVICES AND METHODS FOR CRIMPING A MEDICAL DEVICE

CROSS-REFERENCE TO RELATED APPLICATIONS

This patent application makes reference to, claims priority to, and claims benefit from U.S. Provisional Application Ser. No. 61/822,601, which was filed on May 13, 2013. The disclosure of Provisional Application Ser. No. 61/822,601 is incorporated herein in its entirety.

BACKGROUND

Field

The present disclosure relates to devices, systems, and methods for crimping a medical device. More specifically, the present disclosure relates to devices, systems, and methods for reducing the diameter of a collapsible heart valve prosthesis to be loaded onto a delivery device.

Background

Minimally invasive approaches have been developed to facilitate catheter-based implantation of valve prostheses in a beating heart, intending to obviate the need for the use of classical sternotomy and cardiopulmonary bypass. An expandable prosthetic valve can be compressed about a catheter, inserted inside a lumen within the body, such as the femoral artery, and delivered to a desired location in the heart.

Heart valve prostheses used in these procedures can have a self-expanding multi-level frame that supports a valve body having a plurality of leaflets. The frame can be contracted during percutaneous transluminal delivery and expanded upon deployment within the native heart valve.

In order to compress the frame of the valve prosthesis, crimping techniques can be employed to transition the prosthesis from its natural expanded state to a compressed state. The compressed prosthesis can then be loaded onto or into a delivery device.

BRIEF SUMMARY

The present disclosure relates to devices, systems, and methods for crimping a heart valve prosthesis. The devices, systems, and methods provide uniform, controlled crimping in "reverse" of standard crimping methods. Reducing the diameter of the prosthesis in this manner allows for minimally invasive delivery to the implantation location.

Generally, the devices, systems, and methods crimp the valve in "reverse." In certain embodiments, a funnel can be advanced over the support arms of the prosthesis first. The support arms can be held prolapsed proximal to the tip by a metal puller tube. A funnel can be pushed over the support arms and advanced over the inlet of the valve. Once the valve is in a straight section of the funnel, or, for example, a barrel attached to the funnel, the funnel section can be detached and advanced over the delivery device. In order to crimp the valve down to match the inner diameter of the outer sheath of the delivery device, a split step funnel can be attached to the straight section or barrel. The inside of the split step can be tapered from the inner diameter of the straight section of the barrel to the inner diameter of the outer sheath of the delivery device. The outer sheath can be advanced to load the valve. As the outer sheath is advanced, it can push the split step funnel and barrel portion such that the valve moves through the tapered step and into the outer sheath of the delivery device.

Some embodiments include a system for crimping a prosthetic valve. The system including a first funnel, a second funnel, a delivery device, and an actuator. The first funnel having a first diameter, a tapered section, and a second diameter smaller than the first diameter. The second funnel having a first diameter, a tapered section, and a second diameter smaller than the first diameter. The delivery device including a strut support and an outer sheath, where at least a portion of the delivery device configured to extend through the first funnel and the second funnel The actuator being configured to attach to the prosthetic valve and pull the prosthetic valve through at least one of the first funnel and the second funnel. The first diameter of the first funnel being larger than the first diameter of the second funnel.

In some embodiments, the outer diameter of the outer sheath is less than or equal to the second diameter of the first funnel and the second diameter of the second funnel.

In some embodiments, the first funnel and the second funnel are releasably connected.

In some embodiments, the system also includes a barrel. The barrel being configured to connect the first funnel to the second funnel In some embodiments, the barrel includes a first attachment portion for releasably engaging the first funnel.

In some embodiments, the actuator is a puller tube, the puller tube being configured to extend through the first funnel and the second funnel In some embodiments, the actuator includes a handle, a channel, and a pull ring. In some embodiments, the actuator also includes at least one wire operatively connected to the pull ring. In some embodiments, the actuator is configured to engage to the second funnel In some embodiments, the actuator is configured to engage to the first diameter of the second funnel In some embodiments, the system also includes a first tube releasably connected to the second diameter of the first funnel, and a second tube releasably connected to the second diameter of the second funnel In some embodiments, the first diameter of the second funnel is configured to receive at least a portion of the first tube.

In some embodiments, the prosthetic valve is a self-expanding valve.

In some embodiments, the outer sheath is configured to slide over the strut support.

Some embodiments include a device for crimping a prosthetic valve. The device including a first funnel, a second funnel, and an actuator. The first funnel having a first diameter, a tapered section, and a second diameter smaller than the first diameter. The second funnel having a first diameter, a tapered section, and a second diameter smaller than the first diameter. The actuator being configured to attach to the prosthetic valve and pull the prosthetic valve through at least one of the first funnel and the second funnel The first funnel and the second funnel being configured to releasably connect to each other and the first diameter of the first funnel being larger than the first diameter of the second funnel.

In some embodiments, the device also includes a barrel. The barrel being configured to connect to the first funnel and the second funnel In some embodiments, the barrel includes a first attachment portion for releasably engaging the first funnel.

In some embodiments, the first funnel is configured to directly connect to the second funnel In some embodiments, the second diameter of the first funnel is configured to engage the second diameter of the second funnel.

In some embodiments, the device also includes a first tube releasably connected to the second diameter of the first funnel, and a second tube releasably connected to the second diameter of the second funnel.

Some embodiments include a method for crimping a prosthetic valve. The method including attaching the prosthetic valve to an actuator; advancing a first funnel over the prosthetic valve such that the prosthetic valve moves through the first funnel, the first funnel comprising a first diameter, a tapered section, and a second diameter smaller than the first diameter; advancing a second funnel over the prosthetic valve such that the prosthetic valve moves into the second funnel and onto a strut support of a delivery device, the second funnel comprising a first diameter, a tapered section, and a second diameter smaller than the first diameter; and advancing an outer sheath of the delivery device over the prosthetic valve on the strut support. The first diameter of the first funnel being larger than the first diameter of the second funnel.

In some embodiments, the actuator is a puller tube. The puller tube being configured to extend through the first funnel and the second funnel.

In some embodiments, the first funnel and the second funnel configured to be releasably connected to a barrel. In some embodiments, the method includes attaching the barrel to the first funnel before advancing the first funnel over the prosthetic valve; and advancing the prosthetic valve through the first funnel and into the barrel. In some embodiments, the method includes disconnecting the barrel from the first funnel after advancing the prosthetic valve into the barrel. In some embodiments, the method includes connecting the second funnel to the barrel before advancing the second funnel over the prosthetic valve.

In some embodiments, the actuator comprises a handle, a channel, and a pull ring. In some embodiments, the actuator also includes at least one wire operatively connected to the pull ring.

In some embodiments, the second diameter of the first funnel is configured to engage the second diameter of the second funnel.

BRIEF DESCRIPTION OF THE DRAWINGS

The accompanying figures, which are incorporate herein, form part of the specification and illustrate embodiments of crimping devices, techniques, and methods for crimping a prosthetic device. Together with the description, the figures explain the principals of and allow for the making and using of the crimping systems and methods described herein. These figures are intended to be illustrative, not limiting. Although the disclosure is generally described in the context of these embodiments, it should be understood that it is not intended to limit the scope of the disclosure to these particular embodiments. In the drawings, like reference number indicate identical or functionally similar elements.

FIG. 4 illustrates parts of a crimping system, according to an embodiment.

FIGS. 14 and 15 illustrate a method of detaching a prosthetic valve from an actuator, according to an embodiment.

DETAILED DESCRIPTION

While the disclosure refers to illustrative embodiments for particular applications, it should be understood that the disclosure is not limited thereto. Modifications can be made to the embodiments described herein without departing from the spirit and scope of the present disclosure. Those skilled in the art with access to this disclosure will recognize additional modifications, applications, and embodiments within the scope of this disclosure and additional fields in which the disclosed examples could be applied. Therefore, the following detailed description is not meant to be limiting. Further, it is understood that the systems and methods described below can be implemented in many different embodiments of hardware. Any actual hardware described is not meant to be limiting. The operation and behavior of the systems and methods presented are described with the understanding that modifications and variations of the embodiments are possible given the level of detail presented.

References to "one embodiment," "an embodiment," "in certain embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Figure 1:
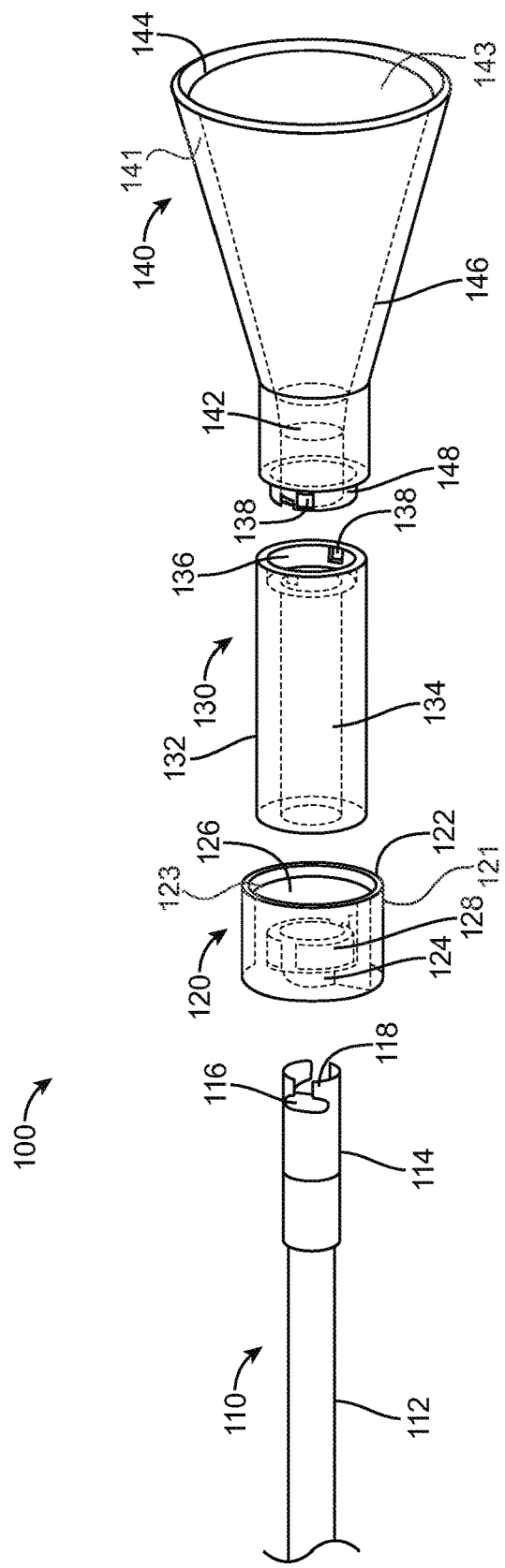
FIG. 1 illustrates parts of a crimping system, according to an embodiment.

FIG. 1 generally illustrates a crimping system 100, according to an embodiment. Crimping system 100 can include a puller tube 110, which can include shaft 112 and tip 114. Tip 114 can include hooks 118 and window 116, to which a prosthetic valve can be attached for loading into the crimping system. Puller tube 110 can be used to pull the prosthetic valve through crimping system 100. Alternatively and/or additionally, puller tube 110 can be used to hold the prosthetic valve stationary while crimping system 100 is advanced over the prosthetic valve. Crimping system 100 can include split step 120. Spilt step may include an outer surface 121 having outer diameter 122 and an interior space 126 having first diameter 123 and second diameter 124, the second diameter 124 being smaller than the first diameter 123. Interior space 126 can also include a tapered region 128. Tapered region 128 can facilitate collapsing the prosthetic valve after it enters first diameter 123 and proceeds towards second diameter 124. In other words, tapered region 128 allows split step 120 to crimp the prosthetic valve. Interior space 126 may also include a straight section 125 located between tapered region 128 and second diameter 124 (see FIG. 6).

Crimping system 100 can also include a barrel 130 having an exterior surface 132 and interior diameter 134. Barrel 130 can include an attachment portion 136, which can include one or more protrusions 138. In certain embodiments, attachment portion 136 can include one or more indentations, in addition to, or instead of, protrusions 138. Crimping system 100 can also include a funnel 140 having an outer surface 141 and an inner surface 143. Inner surface 143 may have a first diameter 144 and a second diameter 142 separated by a tapered region 146, the second diameter 142 being smaller than the first diameter 144. The first diameter 144 of funnel 140 also being larger than the first diameter 123 of split step 120. Funnel 140 can also include an attachment portion 148 having one or more protrusions 138 for releasably engaging protrusions 138 on attachment portion 136. In certain embodiments, attachment portion 148 can include one or more indentations, in addition to, or instead of, protrusions 138. Protrusions 138 on attachment portions 136 and 148 of barrel 130 and funnel 140, respectively, can facilitate mating of barrel 130 to funnel 140. In certain embodiments, attachment portions 136 and 148 may include a luer-lock attachment configuration. In some embodiments, the second diameter 142 of funnel 140 is the same as first diameter 123 of split step 120.

Figure 2:
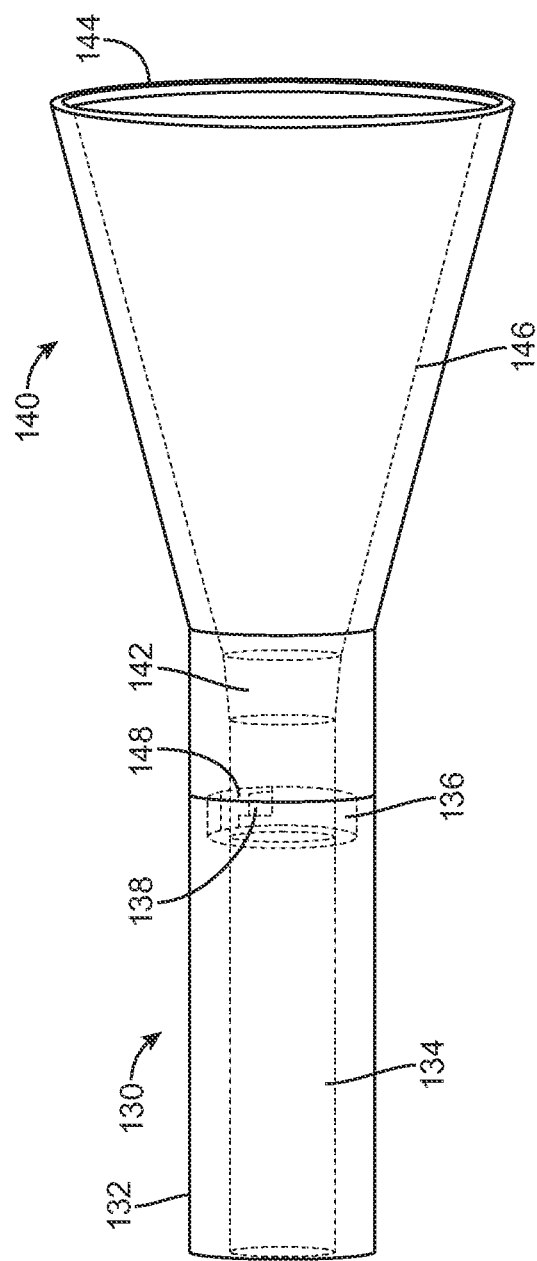
FIG. 2 illustrates a funnel and barrel of a crimping system, according to an embodiment.

FIG. 2 illustrates funnel 140, having second diameter 142, first diameter 144, tapered region 146, and attachment portion 148. FIG. 2 also illustrates barrel 130, having exterior surface 132, interior diameter 134, attachment portion 136, and protrusion 138. As shown in FIG. 2, funnel 140 can be connected to barrel 130. Funnel 140 can be connected to barrel 130 by a variety of means. For example, funnel 140 can be press-fit into barrel 130 such that attachment portion 148 of funnel 140 mates with attachment portion 136 of barrel 130. In certain embodiments, one or more protrusions 138 on attachment portion 136 of barrel 130 can interact with one or more protrusions 138 or indentations of attachment portion 148 of funnel 140. In certain embodiments, funnel 140 and barrel 130 can be twisted in order to have protrusions 138 lock barrel 130 and funnel 140 together. In certain embodiments, barrel 130 and funnel 140 can be correspondingly threaded such that the components can be mated by rotating them in opposite directions.

Figure 3:
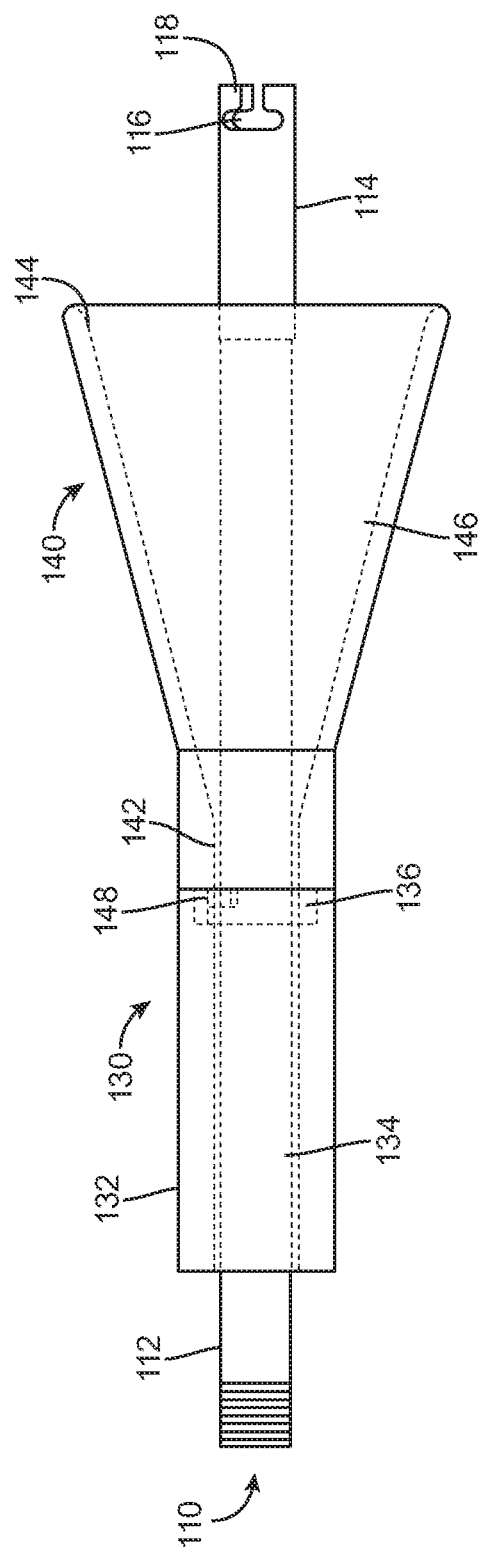
FIG. 3 illustrates parts of a crimping system, according to an embodiment.

FIG. 3 illustrates puller tube 110, which can include shaft 112, tip 114, window 116, and hooks 118. FIG. 3 also illustrates barrel 130 and funnel 140, having parts corresponding to those described above with respect to FIG. 2. Puller tube 110 can be inserted through interior diameter 134 of barrel 130 and through funnel 140. Tip 114 of puller tube 110 can extend out of first diameter 144 of funnel 140 for easy attachment to a valve prosthesis. In certain embodiments, the valve prosthesis (not shown) can be attached to tip 114 of puller tube 110 using hooks 118 and window 116. In certain embodiments, one or more portions of the frame of the prosthesis can be attached to hooks 118 and held within window 116. In certain embodiments, support arms of the prosthesis can be attached to hooks 118 and held within window 116. Hooks 118 and window 116 can have various shapes and configurations designed to retain the valve prosthesis, and are not limited to the configurations shown in the Figures.

In certain embodiments, after the prosthetic valve is connected to puller tube 110, funnel 140 can be advanced over the prosthetic valve (or the prosthetic valve can be pulled into funnel 140 using puller tube 110) such that the prosthetic valve enters first diameter 144 of funnel 140 and proceeds into tapered region 146, where the prosthetic valve can be compressed. Funnel 140 can be further advanced such that the prosthetic valve enters second diameter 142 of funnel 140 and proceeds into interior diameter 134 of barrel 130. Once the prosthetic valve is located within interior diameter 134 of barrel 130, funnel 140 can be disconnected from barrel 130, as shown, for example, in FIG. 4. In some embodiments, interior diameter 134 of barrel 130 is equal to the second diameter 142 of funnel 140. In some embodiments, the length of barrel 130 is such that is it capable of housing the entire valve prosthesis.

Figure 5:
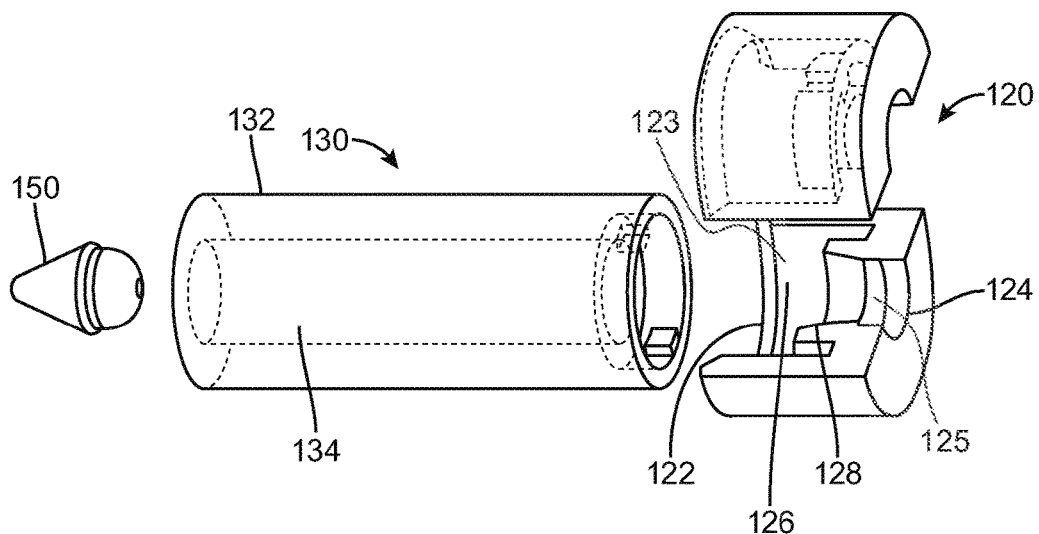
FIG. 5 illustrates parts of a crimping system, according to an embodiment.
Figure 6:
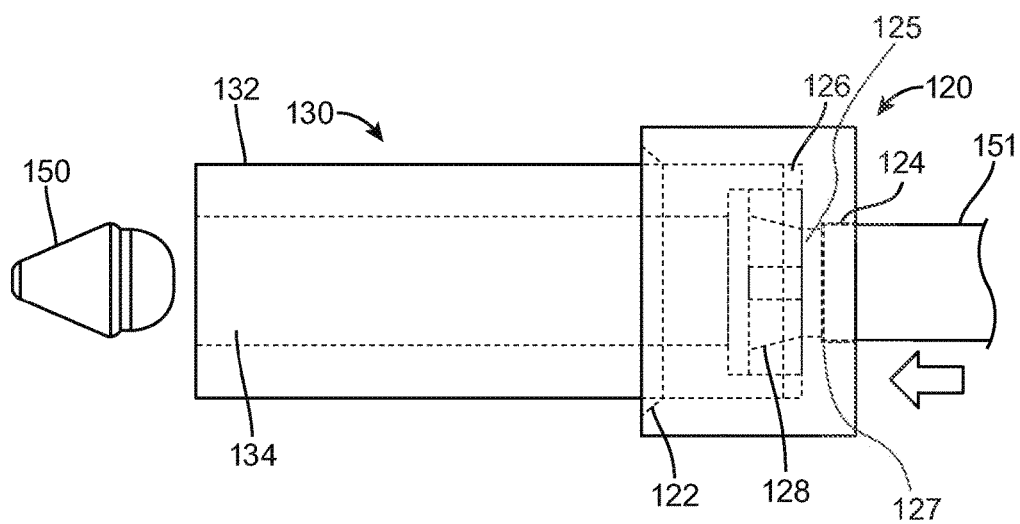
FIG. 6 illustrates parts of a crimping system, according to an embodiment.

FIGS. 5 and 6 illustrate split step 120, which can be used to further decrease the loading diameter of the valve prosthesis. In certain embodiments, split step 120 can be attached to barrel 130 after funnel 140 is disconnected from barrel 130. Delivery device tip 150 is illustrated as a reference point to indicate the distal end of the delivery device (not shown), about which the prosthetic valve can be loaded. In certain embodiments, split step 120 can be fitted about barrel 130. For example, first diameter 123 of split step 120 can be sized to fit about exterior surface 132 of barrel 130. Split step 120 may be configured to split into two pieces as shown in FIG. 5. This allows split step 120 to be fitted about exterior surface 132 of barrel 130 when a delivery device is present and extending through barrel 130. This also allows split step 120 to be fitted about exterior surface 132 of barrel 130 when puller tube 110 is attached to the valve prosthesis and extending through second diameter 124. Preferably, second diameter 124 and/or the diameter of straight section 125 of split step 120 are smaller than second diameter 142 of funnel 140 and interior diameter 134 of barrel 130. This allows the prosthetic valve to be further crimped by split step 120 before it is loaded onto the delivery device.

In certain embodiments, the delivery device can be manipulated to move an outer sheath 151 in the distal direction, as indicated by the arrow in FIG. 6. This can, in turn, advance split step 120 and barrel 130 in the distal direction, enabling the prosthetic valve to enter split step 120 through first diameter 123 and move through interior space 126 and tapered region 128 of split step 120. Second diameter 124 may be configured to receive at least a portion of outer sheath 151. As outer sheath 151 is moved in the distal direction, outer sheath 151 receives valve prosthesis from straight section 125. In certain embodiments, outer sheath 151 can have a diameter approximately equal to second diameter 124 of split step 120, and a distal end of outer sheath 151 can be fitted against a shoulder 127 created by straight section 125 and second diameter 124 to allow the prosthesis to smoothly enter into outer sheath 151. After the outer sheath 151 has received the entire valve prosthesis, split step 120 and barrel 130 can be removed from the delivery device, leaving the valve prosthesis encapsulated within outer sheath 151 of the delivery device with tip 150 sealing the end of outer sheath 151. In certain embodiments, outer sheath 151 can slide within split step 120 and barrel 130 to encapsulate the valve prosthesis. In such embodiments, the outer sheath 151 can have a diameter approximately equal to or less than the diameter of straight section 125 and interior diameter 134 of barrel 130.

In general terms the "valve prosthesis" or "prosthetic valve" of the present disclosure includes a stent or stent frame maintaining a valve structure (tissue or synthetic), with the stent having a natural or normal, expanded arrangement and collapsible to a compressed arrangement for loading within a delivery device. The stent is normally constructed to self-deploy or self-expand when released from a delivery device. For example, the stented prosthetic heart valve useful with the present disclosure can be a prosthetic valve sold under the trade name CoreValve® available from Medtronic CoreValve, LLC. Other non-limiting examples of transcatheter heart valve prostheses useful with systems, devices, and methods of the present disclosure are described in U.S. Publication Nos. 2006/0265056; 2007/0239266; and 2007/0239269, the teachings of each which are incorporated herein by reference. Another non-limiting example of prosthetic valves that may be used in accordance with one or more embodiments of the devices and methods of the present disclosure are described in more detail in U.S. patent application Ser. No. 14/175,100, filed on Feb. 7, 2014, entitled HEART VALVE PROSTHESIS, which is incorporated herein by reference. The stents or stent frames are support structures that comprise a number of struts or wire portions arranged relative to each other to provide a desired compressibility and strength to the prosthetic heart valve. In general terms, the stents or stent frames of the present disclosure are generally tubular support structures having an internal area in which valve structure leaflets will be secured. The leaflets can be formed from a verity of materials, such as autologous tissue, xenograph material, or synthetics as are known in the art. The leaflets may be provided as a homogenous, biological valve structure, such as porcine, bovine, or equine valves. Alternatively, the leaflets can be provided independent of one another (e.g., bovine or equine paracardial leaflets) and subsequently assembled to the support structure of the stent frame. In another alternative, the stent frame and leaflets can be fabricated at the same time, such as may be accomplished using high-strength nano-manufactured NiTi films produced at Advance BioProsthetic Surfaces (ABPS), for example. The stent frame support structures are generally configured to accommodate at least two (typically three) leaflets; however, replacement prosthetic heart valves of the types described herein can incorporate more or less than three leaflets.

Some embodiments of the stent frames can be a series of wires or wire segments arranged such that they are capable of self-transitioning from the compressed or collapsed arrangement to the normal, radially expanded arrangement. In some constructions, a number of individual wires comprising the stent frame support structure can be formed of a metal or other material. These wires are arranged in such a way that the stent frame support structure allows for folding or compressing or crimping to the compressed arrangement in which the internal diameter is smaller than the internal diameter when in the natural, expanded arrangement. In the collapsed arrangement, such a stent frame support structure with attached valves can be mounted onto a delivery device. The stent frame support structures are configured so that they can be changed to their natural, expanded arrangement when desired, such as by the relative movement of one or more sheaths relative to a length of the stent frame.

The wires of the stent frame support structures in embodiments of the present disclosure can be formed from a shape memory material such as a nickel titanium alloy (e.g., Nitinol™). With this material, the support structure is self-expandable from the compressed arrangement to the natural, expanded arrangement, such as by the application of heat, energy, and the like, or by the removal of external forces (e.g., compressive forces). This stent frame support structure can also be compressed and re-expanded multiple times without damaging the structure of the stent frame. In addition, the stent frame support structure of such an embodiment may be laser-cut from a single piece of material or may be assembled from a number of different components. For these types of stent frame structures, one example of a delivery device that can be used includes a catheter with a retractable sheath that covers the stent frame until it is to be deployed, at which point the sheath can be retracted to allow the stent frame to self-expand.

Figure 7:
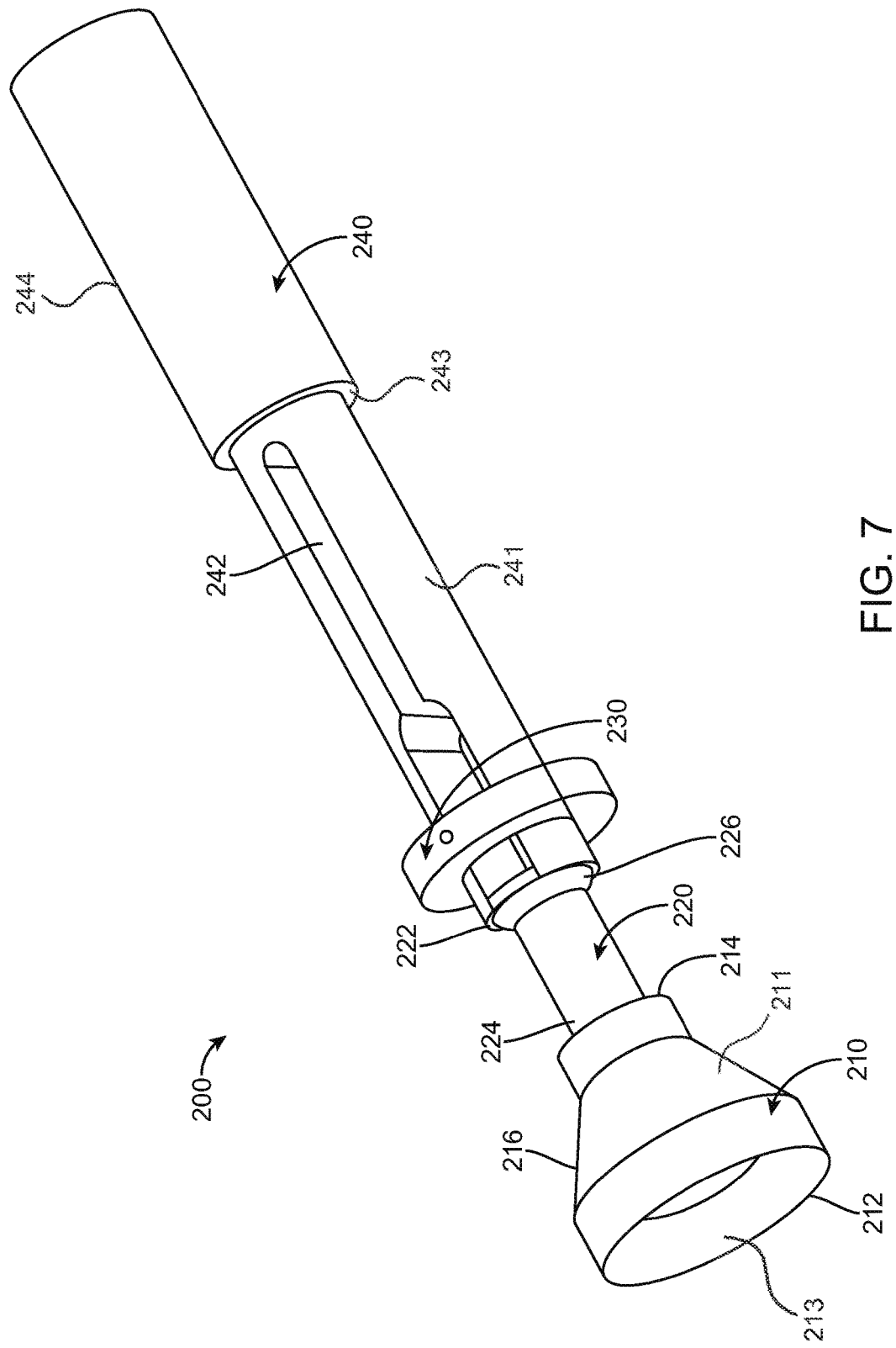
FIG. 7 illustrates a crimping system, according to an embodiment.

FIGS. 7-22 illustrate a crimping system, according to an embodiment. FIG. 7 illustrates a crimping system 200, which can include a handle 240 having a channel 242 and a pull ring 230. Handle 240 may be configured to receive at least a portion of a delivery device 250. Crimping system 200 can include a small funnel 220 having an outer surface 221 and an inner surface 223. Inner surface 223 can have first diameter 222 and a second diameter 224 separated by a tapered region 226, the second diameter 224 being smaller than the first diameter 222. Crimping system 200 can also include a large funnel 210 having outer surface 211 and an inner surface 213. The term "large" meaning that at least a portion of inner surface 213 has a diameter larger than the largest diameter of inner surface 223 of small funnel 220. Inner surface 213 can include a first diameter 212 and a second diameter 214 separated by a tapered region 216, the second diameter 214 being smaller than the first diameter 212. Preferably, first diameter 212 of large funnel 210 is larger than first diameter 222 of small funnel 220. In certain embodiments, second diameter 214 of large funnel 210 can be sized to mate with and directly connect to second diameter 224 of small funnel 220. In some embodiments, second diameter 214 of large funnel 210 is equal to second diameter 224 of small funnel 220.

Figure 8:
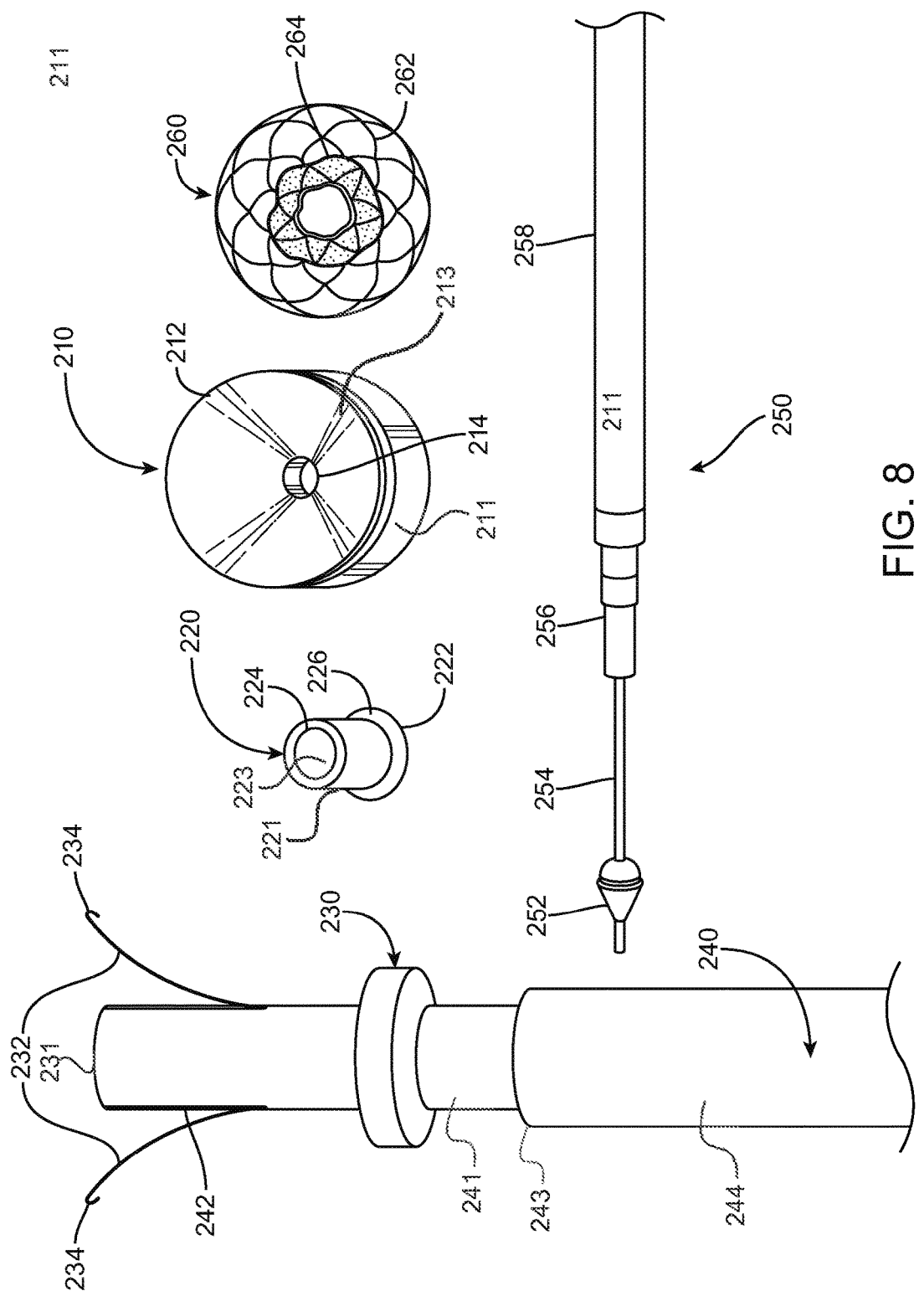
FIG. 8 illustrates parts of a crimping system and a prosthetic valve, according to an embodiment.

FIG. 8 shows a deconstructed parts assembly of crimping system 200, according to an embodiment. Handle 240 can include a body 244 and an elongated portion 241 connected via a shoulder 243. Pull ring 230 can be slidably disposed on elongated portion 241. Elongated portion 241 can include a distal end configure to engage first diameter 222 of small funnel 220. Handle 240 can include channel 242 extending through and located on elongated portion 241, from which pull wires 232 can be extend. In certain embodiments, pull wires 232 can have hooks 234 located at an end of pull wires 232. Pull wires 232 can be operatively connected to pull ring 230 such that pull ring 230 can retract and extend pull wires 232 into and out of elongated portion 241 and channel 242. FIG. 8 also illustrates small funnel 220 having a hollow shape defined by first diameter 222, second diameter 224, and tapered region 226. As shown in FIG. 8, large funnel 210 can include a hollow shape defined by first diameter 212, second diameter 214, and tapered region 216 (shown in FIG. 7).

FIG. 8 also illustrates a prosthetic valve 260, according to an embodiment. Prosthetic valve 260 can include a frame 262 and a valve portion 264. FIG. 8 further illustrates delivery device 250, according to an embodiment. Delivery device 250 can include an outer sheath 258, a strut support 256, an inner shaft 254, and a tip 252.

Figure 9:
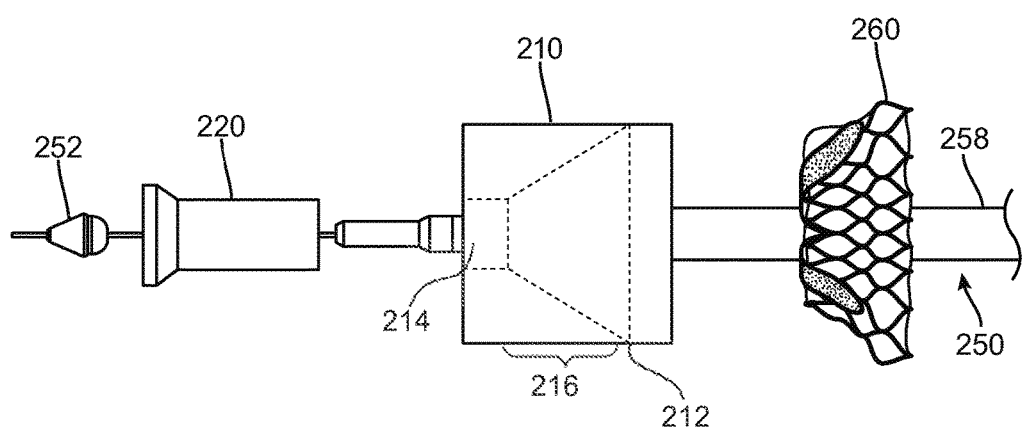
FIG. 9 illustrates parts of a crimping system and a prosthetic valve loaded onto a delivery device, according to an embodiment.

FIG. 9 illustrates prosthetic valve 260, large funnel 210, and small funnel 220 loaded onto delivery device 250 having outer sheath 258 located at a proximal end and tip 252 located at a distal end. Small funnel 220 can be moved along delivery device 250 to be fitted against or within large funnel 210.

Figure 10:
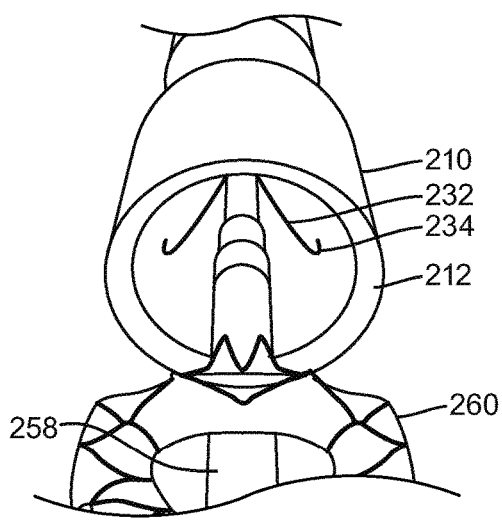
FIGS. 10 and 11 illustrate a method of attaching a prosthetic valve to a crimping system, according to an embodiment.
Figure 11:
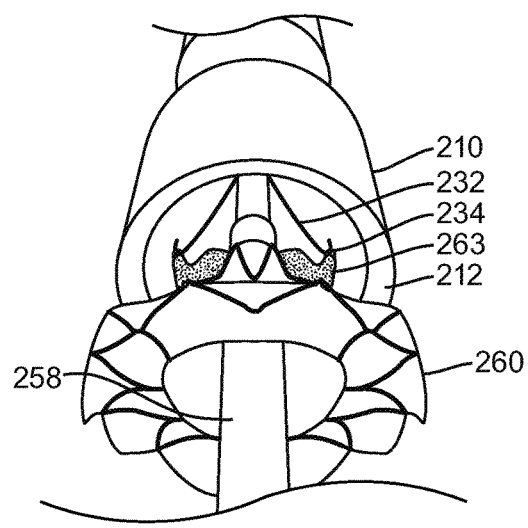
Figure 12:
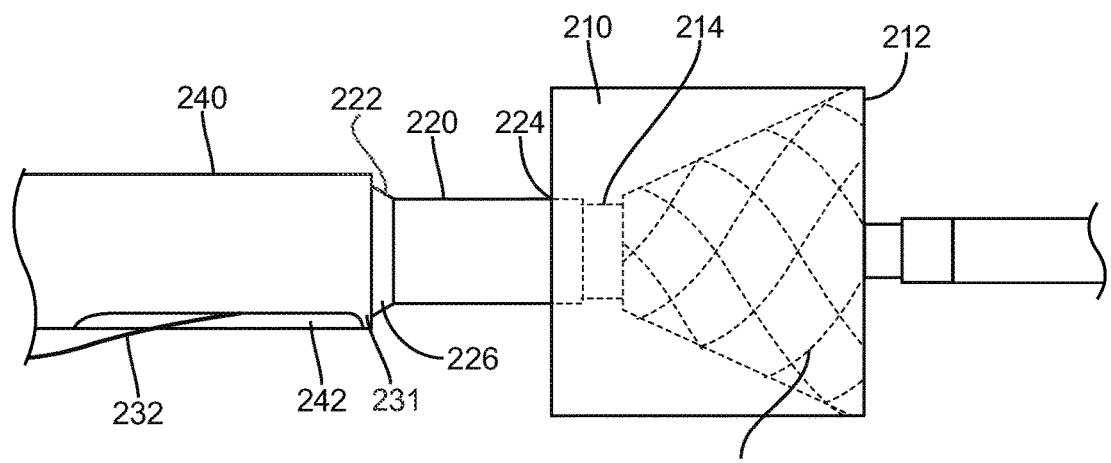
FIGS. 12 and 13 illustrate a method of loading a prosthetic valve into a funnel of a crimping system, according to an embodiment.
Figure 13:
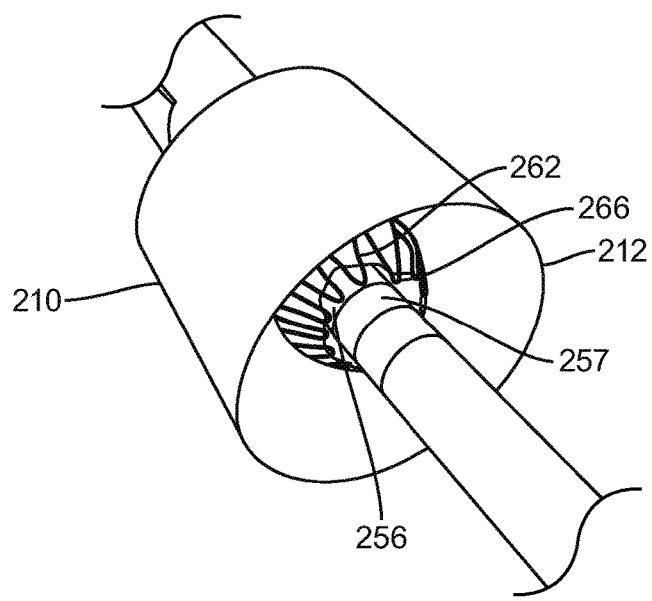

FIGS. 10 and 11 illustrate a method of attaching prosthetic valve 260 to the handle 240, according to an embodiment. As shown in FIG. 12, distal end 231 of elongated portion 241 can engage first diameter 222 of small funnel 220. Pull wires 232 can be compressed and inserted through small funnel 220 and large funnel 210. Pull ring 230 may be configured to extend pull wires 232 out of distal end 231, through small funnel 220 and through large funnel 210. Prosthetic valve 260 can be moved along outer sheath 258 until at least a portion of the prosthetic valve is in the vicinity of pull wires 232, e.g., until support arms 263 of prosthetic valve 260 are in the vicinity of pull wires 232 (as shown in FIG. 11). A portion of frame 262, e.g., support arms 263 can be attached to hooks 234 of pull wires 232, for example, by folding support arms 263 in the distal direction.

FIGS. 12-22 illustrate the crimping process, according to an embodiment. In certain embodiments, once hooks 234 of pull wires 232 are attached to support arms 263, pull ring 230 can be moved in a direction away from large funnel 210 such that prosthetic valve 260 is pulled into large funnel 210 through first diameter 212, as shown, for example, in FIG. 12. In certain embodiments, as shown, for example, in FIG. 13, tabs 266 of frame 262 can be positioned about strut support 256 and landing zone 257 of delivery device 250. As shown in FIG. 14, in certain embodiments, pull ring 230 can be moved along handle 240 in a direction further away from large funnel 210 and small funnel 220, as indicated by the arrow. In certain embodiments, a stopper can be included in or on handle 240 to stop pull ring 230 at a certain location. In some embodiments, shoulder 243 can serve as the stopper. Pull ring 230 can be moved away from large funnel 210 and small funnel 220 until prosthetic valve 260 is located at least partially within small funnel 220. In certain embodiments, a portion of frame 262 such as support arms 263 can extend out of small funnel 220 and into channel 242 of handle 240. Pull ring 230 can then be advanced toward small funnel 220 in order to release hooks 234 of pull wires 232 from support arms 263 of frame 262 of prosthetic valve 260. In certain embodiments, pull wires 232 can be manually released from support arms 263 of frame 262.

Figure 16:
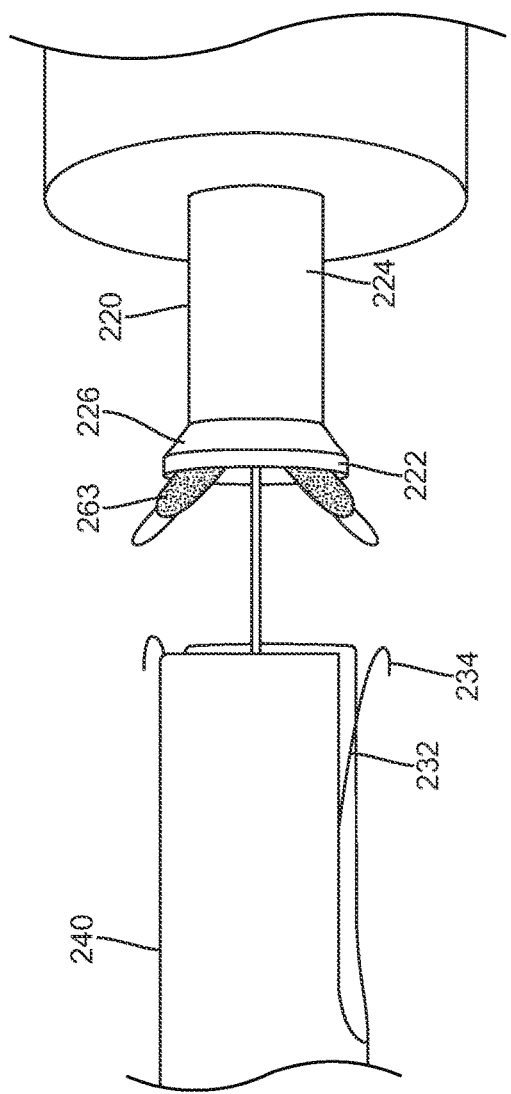
FIGS. 16 and 17 illustrate a prosthetic valve loaded into a funnel, according to an embodiment.
Figure 17:
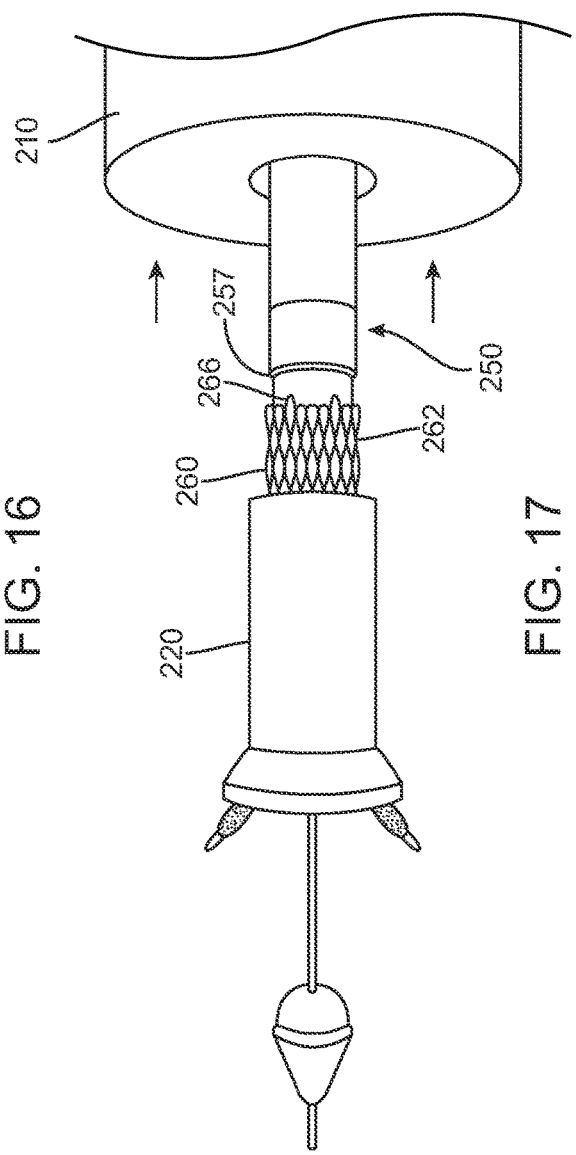
Figure 18:
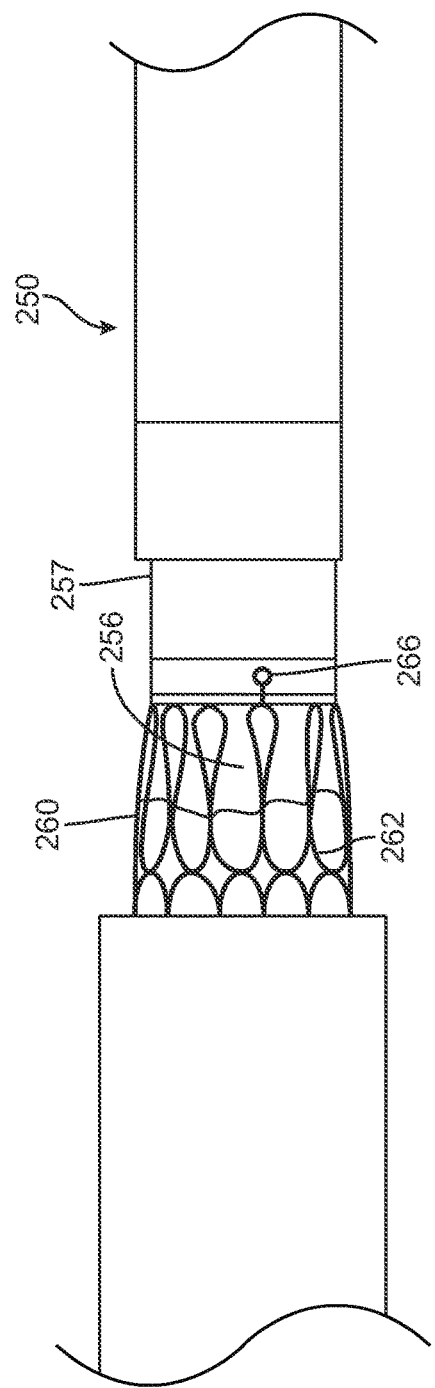
FIG. 18 illustrates a method of attaching a prosthetic valve to a delivery device, according to an embodiment.
Figure 19:
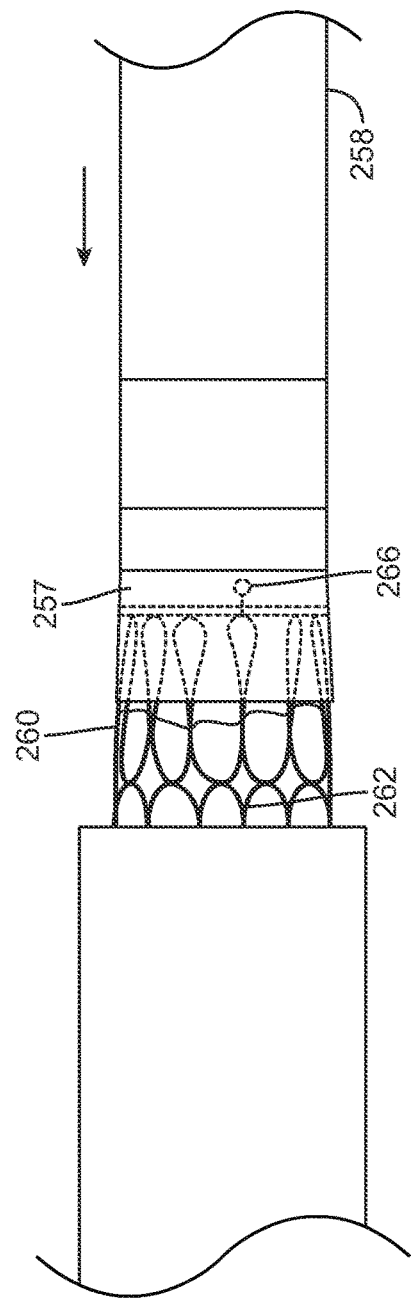
FIG. 19 illustrates covering a prosthetic valve with an outer sheath of the delivery device, according to an embodiment.

As shown in FIG. 16, once hooks 234 of pull wires 232 are released from support arms 263 of frame 262, handle 240 can be removed, leaving support arms 263 of frame 262 exposed out of first diameter 222 and tapered region 226 of small funnel 220. The majority of prosthetic valve 260 can be constrained within second diameter 224 of small funnel 220. As shown, for example, in FIG. 17, large funnel 210 can also be removed by sliding it along delivery device 250 in the direction indicated by the arrows. This can leave prosthetic valve 260 loaded within small funnel 220 with frame 262 partially exposed. After large funnel 210 is removed frame 262 of prosthetic valve 260 can remain compressed and frictionally engaged to small funnel 220 and/or strut support 256. In such embodiments, frame 262 can be collapsed about strut support 256 so as to engage strut support 256 and/or landing zone 257. Tabs 266 can be aligned with landing zone 257. In certain embodiments, tabs 266 of frame 262 can be attached to landing zone 257 using for example, but not limited to, a tongue and groove mechanism, a keyhole and pin mechanism, a hook and releasable lanyard mechanism or similar mechanisms. Once prosthetic valve 260 is secured to delivery device 250, outer sheath 258 can be moved over landing zone 257, tabs 266, and frame 262 of prosthetic valve 260 in the direction indicated by the arrow in FIG. 19.

Figure 20:
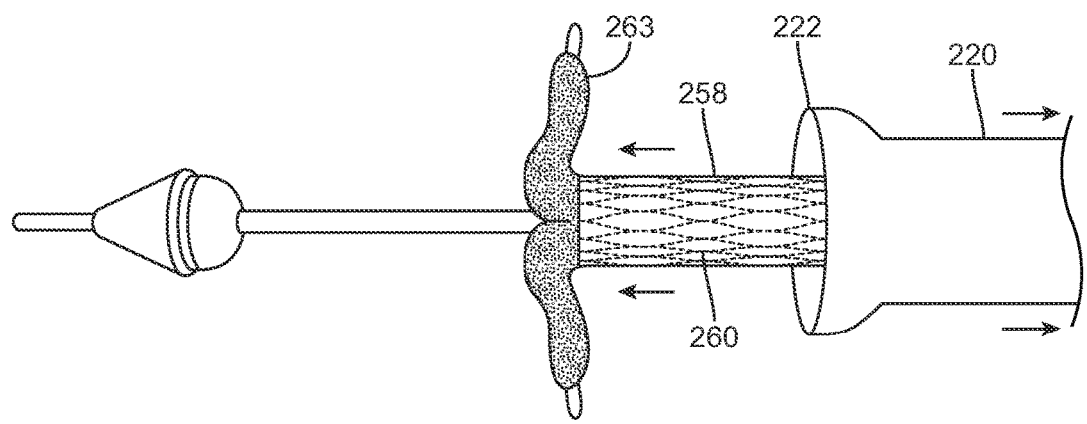
FIGS. 20-22 illustrate a method of loading a prosthetic valve within an outer sheath of the delivery device, according to an embodiment.
Figure 21:
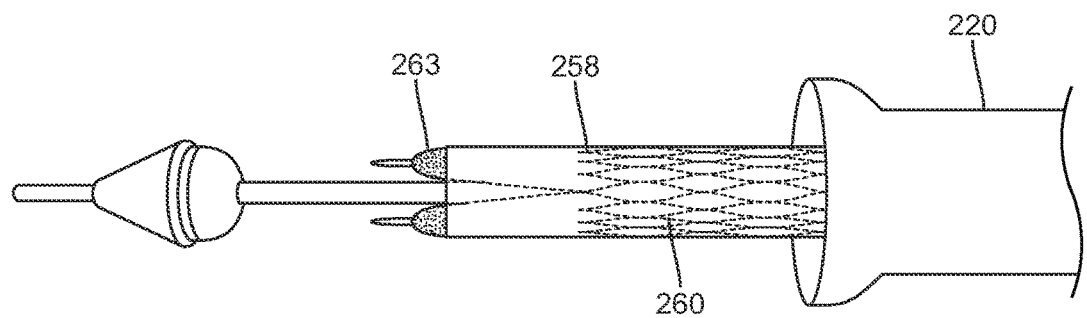
Figure 22:
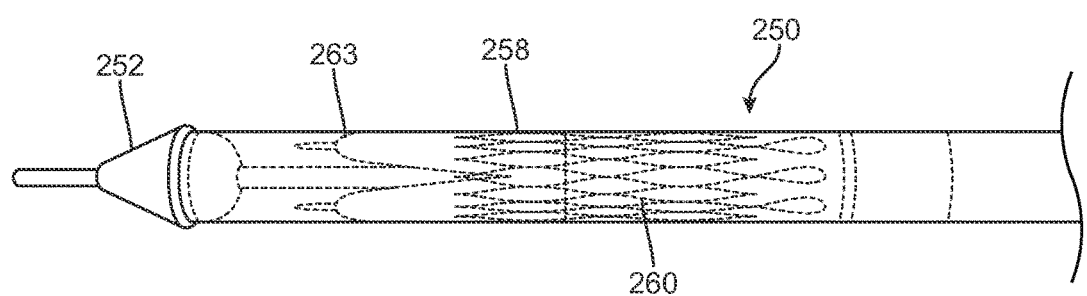

FIGS. 20-22 illustrate the completion of loading prosthetic valve 260 within outer sheath 258 according to one embodiment. As shown in FIG. 20, outer sheath 258 can be advanced through small funnel 220 and out of first diameter 222 to further constrain prosthetic valve 260. Small funnel 220 can be removed in an opposite direction to uncover and visualize prosthetic valve 260. In FIG. 20, support arms 263 are shown in an unconstrained configuration. FIG. 21 illustrates support arms 263 being collapsed and enclosed within outer sheath 258. Finally, FIG. 22 illustrates the entire prosthetic valve 260 encapsulated within outer sheath 258 as outer sheath 258 reaches tip 252 of delivery device 250.

FIGS. 23-32 illustrate a crimping system 300, according to an embodiment. Crimping system 300 can include a puller tube 310 having a shaft 312 and one or more hooks 318. Crimping system 300 can include a small funnel 320 having a through hole 324 extending from a proximal end 321 to a distal end 323. Proximal end 321 can have a first inner diameter and distal end 323 can have a second inner diameter, the first inner diameter being separated from the second inner diameter by tapered region 326 and the first inner diameter being larger than the second inner diameter. Small funnel 320 can include a small tube 322 releasably attached to distal end 323 via one or more attachment members 328. Crimping system 300 can include a large funnel 330 having a through hole 334 extending from a proximal end 331 to a distal end 333. Proximal end 331 can have a first inner diameter and distal end 333 can have a second inner diameter, the first inner diameter and the second inner diameter being separated by a tapered region 336 and the first inner diameter being larger than the second inner diameter.

Figure 23:
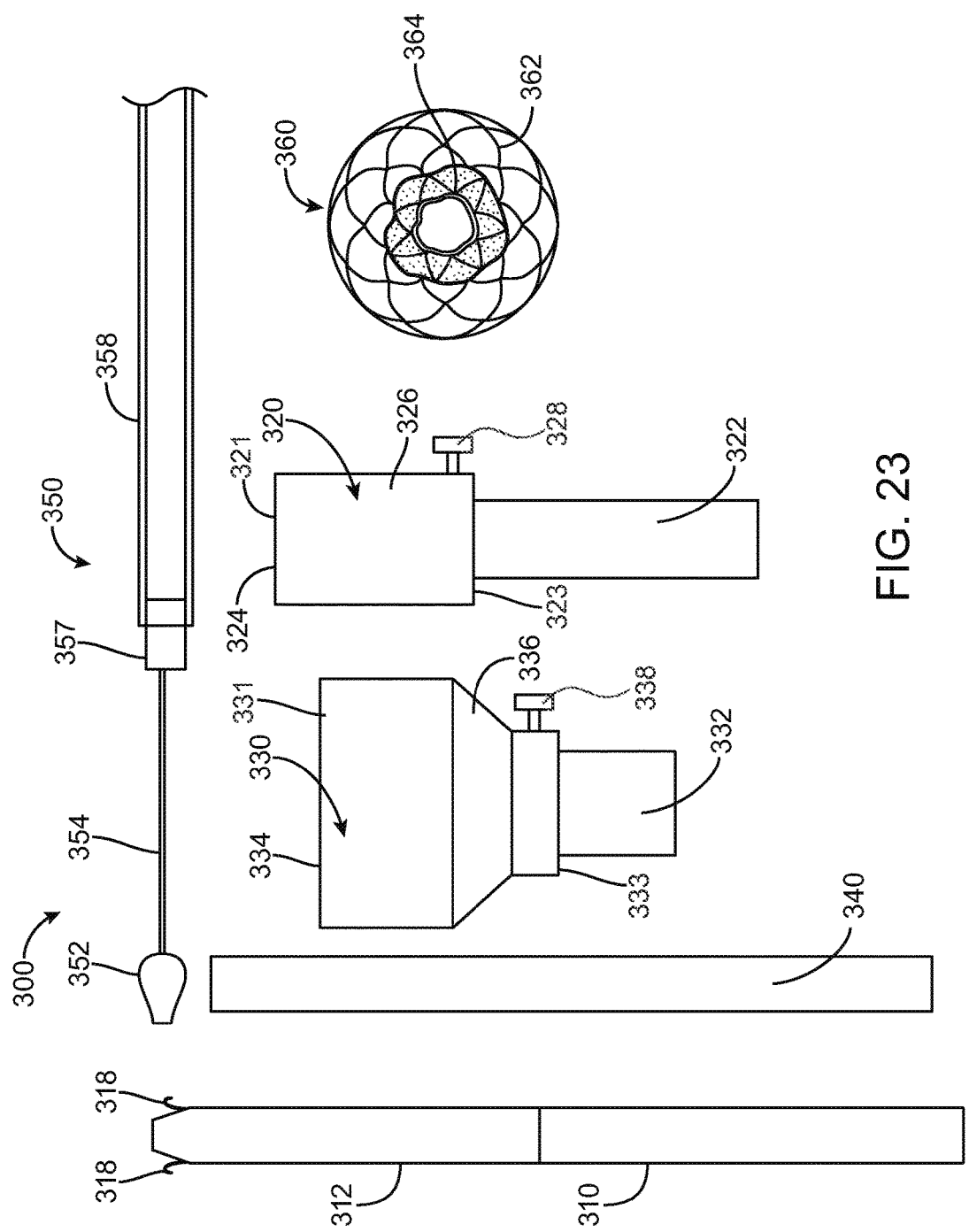
FIG. 23 illustrates parts of a crimping system and a prosthetic valve, according to an embodiment.

Compared to small funnel 320, at least a portion of the interior diameter of large funnel 330 is larger than the largest interior diameter of small funnel 320. Preferably, proximal end 331 of large funnel 330 has an inner diameter that is larger than the inner diameter of proximal end 321 of small funnel 320. Large funnel 330 can include a large tube 332 releasably attached to distal end 333 via one or more attachment members 338. Large tube 332 has a larger inner diameter than the inner diameter of small tube 322. Crimping system 300 can also include a support tube 340. Also shown in FIG. 23 is a delivery device 350, according to an embodiment. Delivery device 350 can include outer sheath 358, landing zone 357, inner shaft 354, and tip 352. FIG. 23 also shows a prosthetic valve 360 having frame 362 and valve portion 364.

While FIG. 23 shows attachment members 328 and 338 attached to the exterior of small funnel 320 and large funnel 330, small funnel 320 and large funnel 330 can include any type of known releasable attachment means. For example, but not limited to, small funnel 320 and large funnel 330 can include screw threads, luer-locks, snap-fitting mechanisms, etc.

Figure 24:
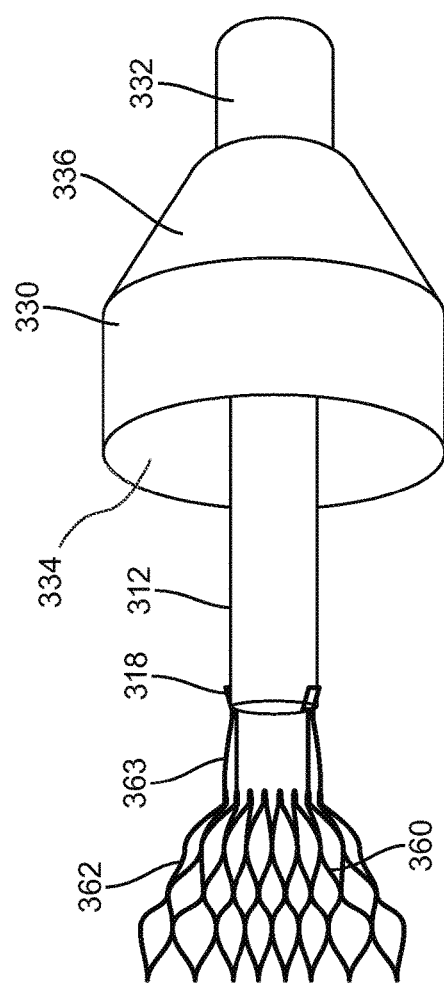
FIG. 24 illustrates a method of attaching a prosthetic valve to a crimping system, according to an embodiment.
Figure 25:
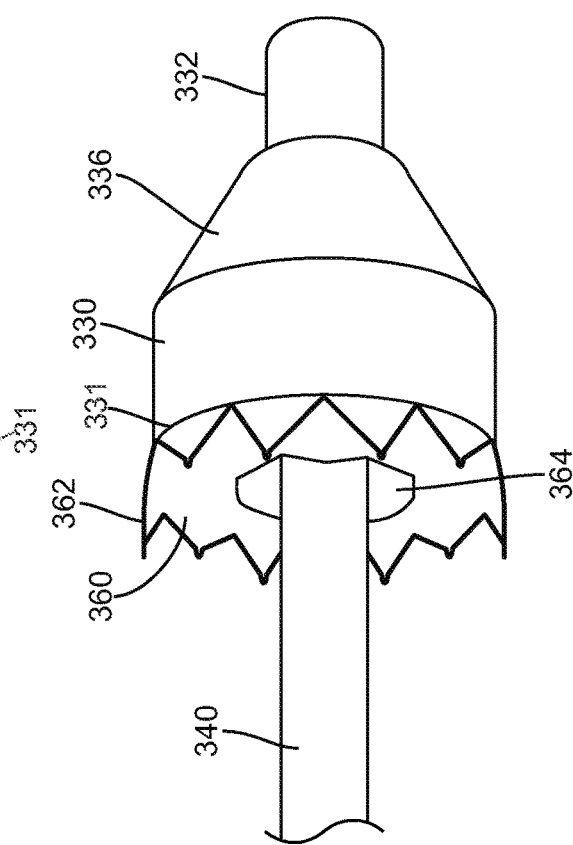
FIG. 25 illustrates a method of loading a prosthetic valve into a funnel of crimping system, according to an embodiment.
Figure 26:
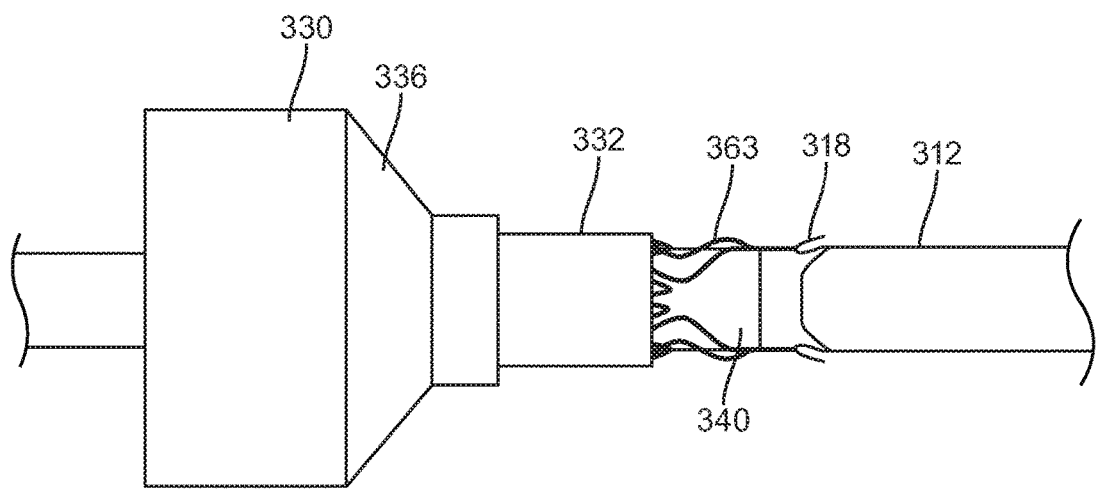
FIG. 26 illustrates a method of loading a prosthetic valve through a funnel, according to an embodiment.
Figure 27:
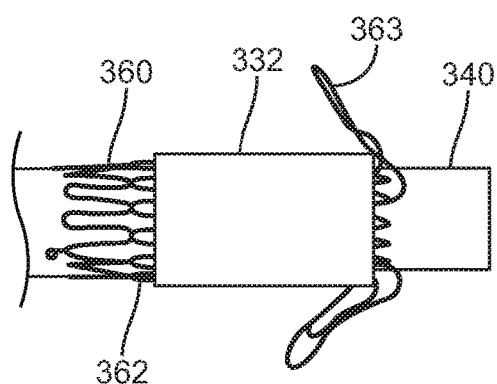
FIG. 27 illustrates a prosthetic valve loaded on a support tube, according to an embodiment.

FIG. 24 illustrates prosthetic valve 360 with support arms 363 extending from frame 362 and attached to hooks 318 of shaft 312. Shaft 312 can extend through large funnel 330 and large tube 332, and out of proximal end 331. Shaft 312 can be used to pull prosthetic valve 360 into proximal end 331 of large funnel 330 and further into tapered region 336 until prosthetic valve 360 enters large tube 332. As shown in FIG. 25, support tube 340 can be inserted through valve portion 364 of prosthetic valve 360 and into large funnel 330 and large tube 332. Prosthetic valve 360 can be pulled through proximal end 331 of large funnel 330, through tapered region 336, and into large tube 332. This can collapse prosthetic valve 360 about support tube 340 until support arms 363 of prosthetic valve 360 are through large tube 332, as shown in FIG. 26. Then, support arms 363 can be disconnected from hooks 318 of shaft 312, and shaft 312 and large funnel 330 can be removed, as shown, for example, in FIG. 27. Once shaft 312 and large funnel 330 are removed, support arms 363 can be allowed to fold back into their native position. Frame 362 of prosthetic valve 360 can generally be located within large tube 332 and about support tube 340. Support tube 340 and/or large tube 332 can be used to hold prosthetic valve 360 in a partially crimped configuration. In some embodiments, as shown in FIGS. 27 and 28, large tube 332 has a length such that at least a portion of prosthetic valve 360 extends from both ends of large tube 332.

Figure 28:
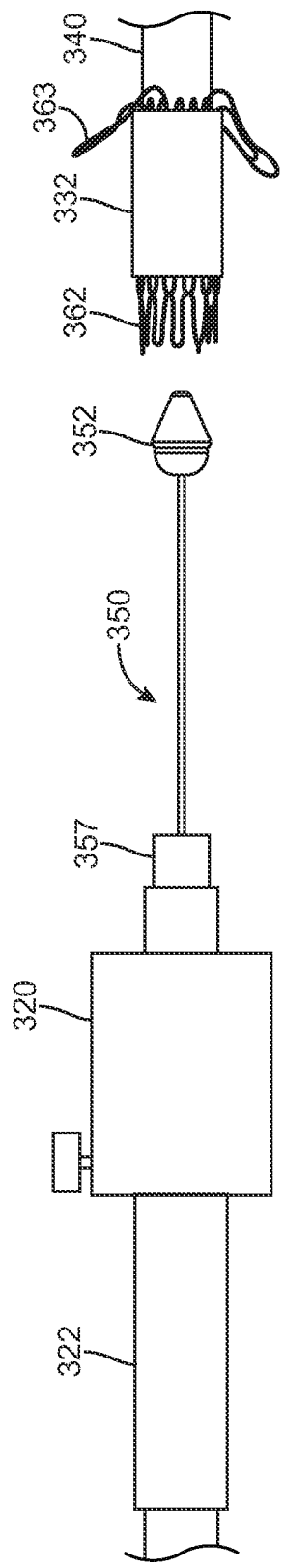
FIG. 28 illustrates a method of loading a prosthetic valve onto a delivery device, according to an embodiment.
Figure 29:
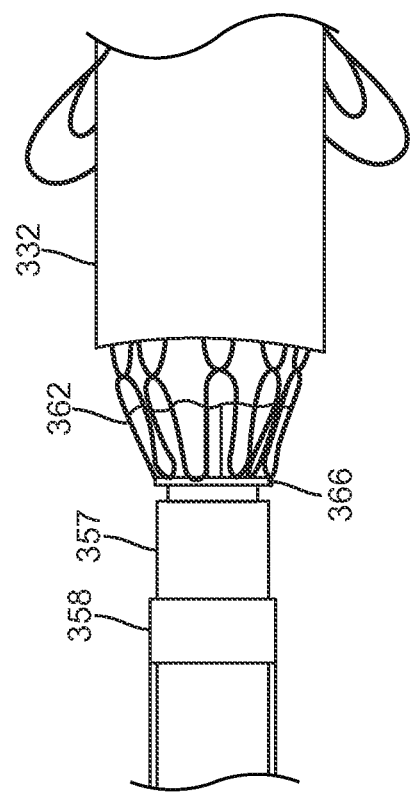
FIG. 29 illustrates a method of attaching a prosthetic valve to delivery device, according to an embodiment.
Figure 30:
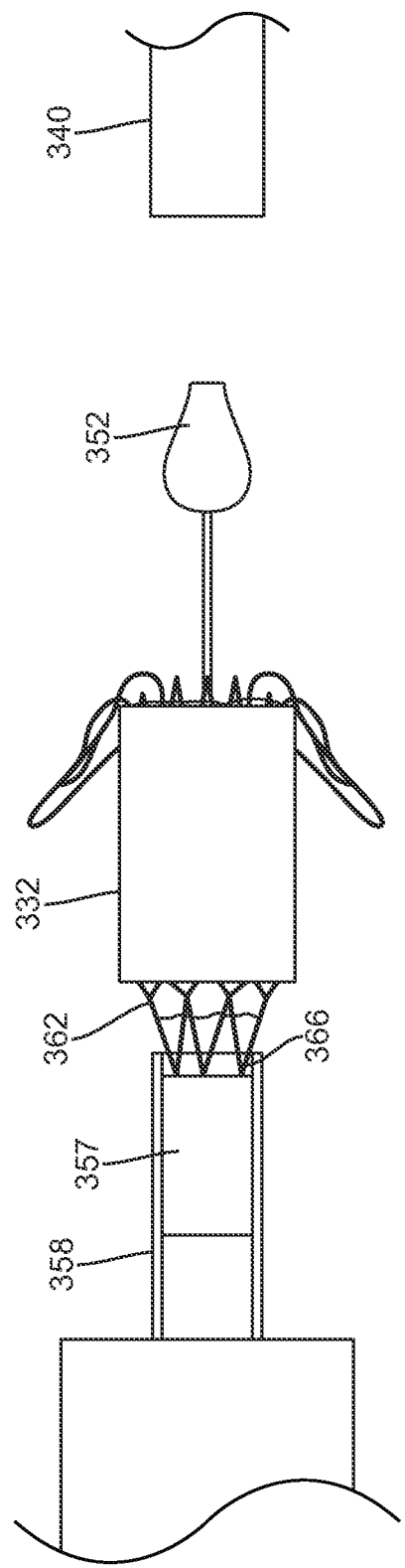
FIG. 30 illustrates a method of loading a prosthetic valve onto a delivery device, according to an embodiment.

As shown in FIG. 28, in some embodiments, small funnel 320 and small tube 322 can be loaded over delivery device 350. Delivery device 350 with small funnel 320 and small tube 322 loaded thereon can then be attached to large tube 332 to further crimp prosthetic valve 360. Tip 352 of delivery device 350 can be inserted through the interior of frame 362, large tube 332, and support tube 340. As shown, for example, in FIG. 29, delivery device 350 can be advanced until landing zone 357 engages a portion of prosthetic valve 360, e.g., tabs 366 of frame 362 near large tube 332. In some embodiments, tabs 366 can be attached to landing zone 357. In certain embodiments, tabs 366 of frame 362 can be attached to landing zone 357 using for example, but not limited to, a tongue and groove mechanism, a keyhole and pin mechanism, a hook and releasable lanyard mechanism, or similar mechanisms. Once a portion of prosthetic valve 360 is attached to landing zone 357, outer sheath 358 can be advanced over at least a portion of frame 362. As shown in FIG. 30, outer sheath 358 can be advanced over landing zone 357 and tabs 366 to secure frame 362 on delivery device 350. As shown in FIG. 30, support tube 340 can be removed over tip 352, leaving frame 362 constrained within large tube 332.

Figure 31:
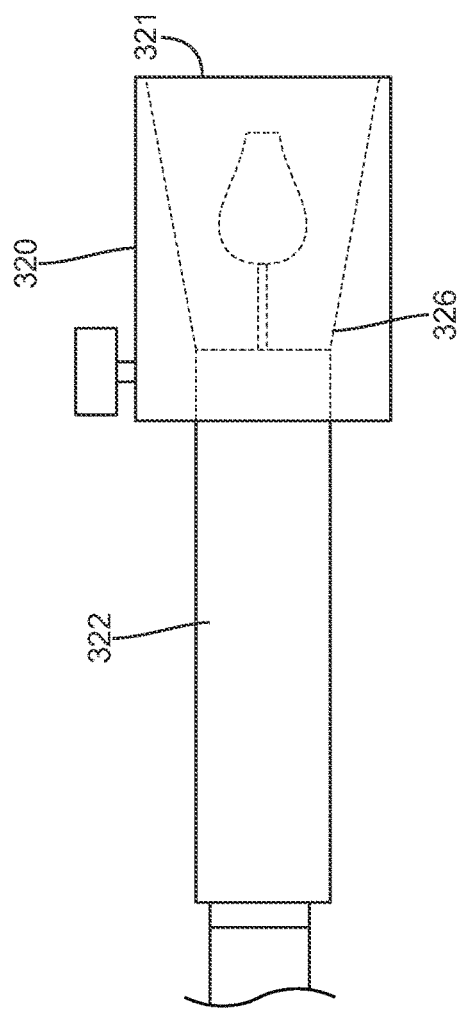
FIG. 31 illustrates a method of loading a prosthetic valve into a funnel attached to a delivery device, according to an embodiment.
Figure 32:
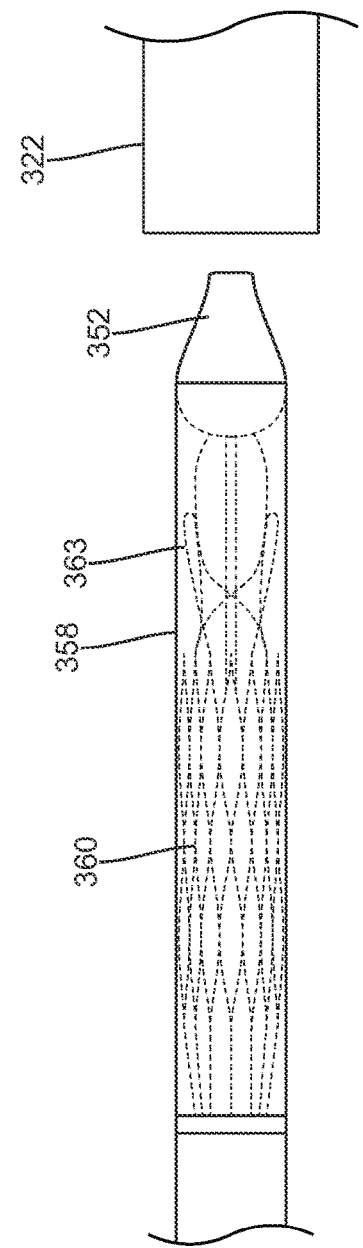
FIG. 32 illustrates a prosthetic valve contained within an outer sheath of a delivery device, according to an embodiment.
Figure 33:
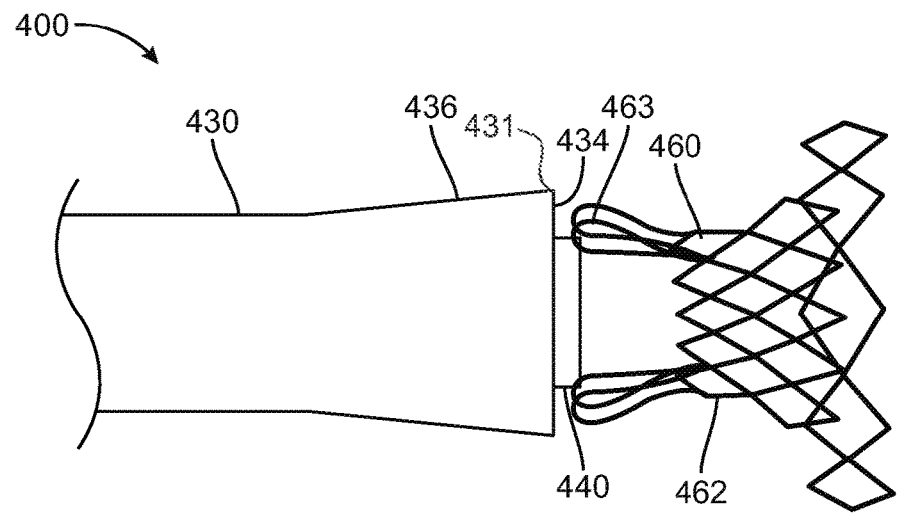
FIG. 33 illustrates a prosthetic valve attached to a crimping device, according to an embodiment.

As shown in FIG. 31, small funnel 320 can be advanced, which can displace large tube 332 such that prosthetic valve 360 moves through proximal end 321, into tapered region 326 of small funnel 320, and then into small tube 322. As small funnel 320 is advanced over prosthetic valve 360 (or prosthetic valve 360 is pulled through small funnel 320), prosthetic valve 360 is further crimped and prosthetic valve 360 is forced into small tube 322. As shown in FIG. 32, outer sheath 358 can be advanced to tip 352 of delivery device 350 to fully encapsulate prosthetic valve 360 and support arms 363 within outer sheath 358 and so that small tube 322 can be removed.

Figure 34:
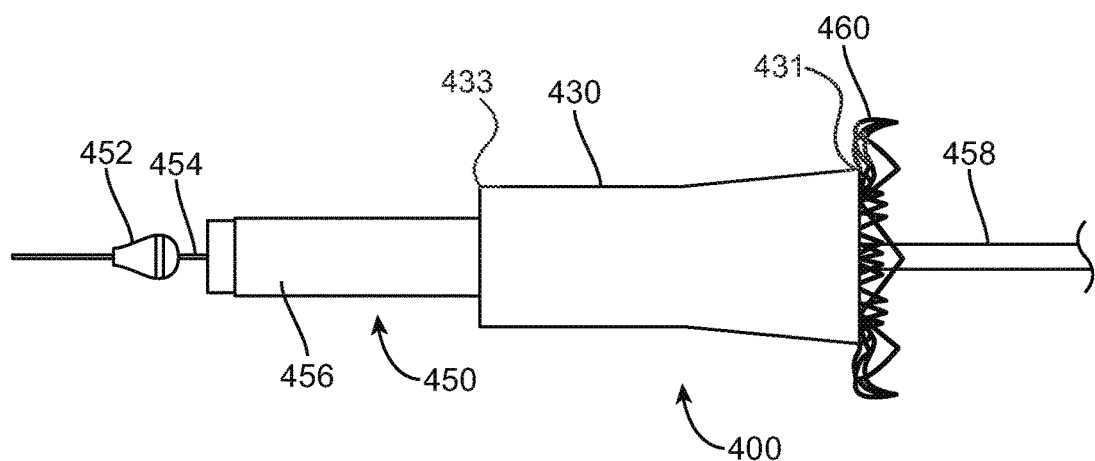
FIG. 34 illustrates a prosthetic valve loaded into a funnel of a crimping device system, according to an embodiment.

FIGS. 33-38 illustrate crimping system 400, according to an embodiment. Crimping system 400 can include a large funnel 430 having a through hole 434 defined by a proximal end 431 having a first diameter and a distal end 433 having a second diameter, proximal end 431 and distal end 433 separated by a tapered region 436 and the first diameter being larger than the second diameter. As shown, for example, in FIG. 33, a portion of prosthetic valve 460, e.g., support arms 463 extending from frame 462 of prosthetic valve 460 can be threaded with suture 440 in preparation for loading into through hole 434 and tapered region 436 of large funnel 430. As shown in FIG. 34, large funnel 430 can be placed over delivery device 450 which can include tip 452, inner shaft 454, retaining tube 456, and outer sheath 458. Then, prosthetic valve 460 can be pulled into large funnel 430 using sutures 440. Alternatively, large funnel 430 can be advanced over prosthetic valve 460 while maintaining tension on sutures 440. As large funnel 430 is advanced over prosthetic valve 460 (or prosthetic valve 460 is pulled through large funnel 430), prosthetic valve 460 is crimped.

Figure 35:
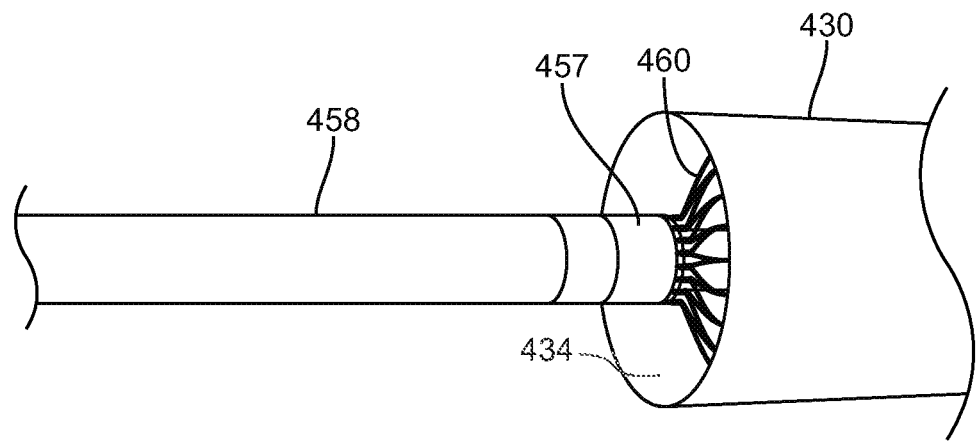
FIG. 35 illustrates a prosthetic valve being pulled through a funnel of a crimping device, according to an embodiment.
Figure 36:
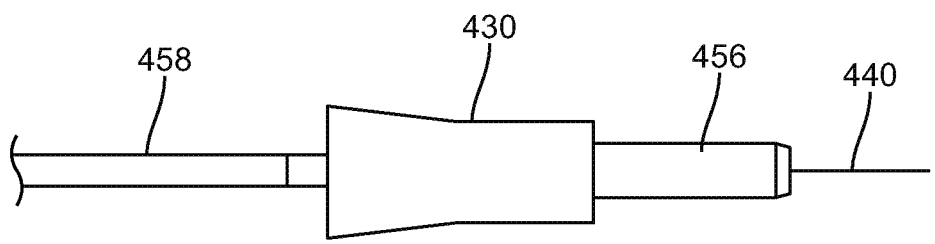
FIGS. 36-38 illustrate a prosthetic valve being loaded onto a delivery device from a crimping system, according to an embodiment.
Figure 37:
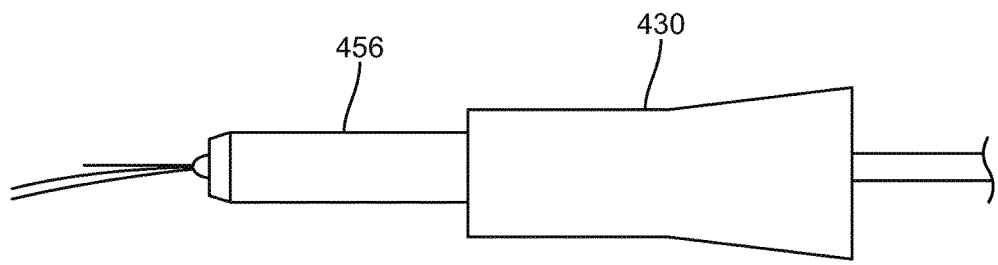
Figure 38:
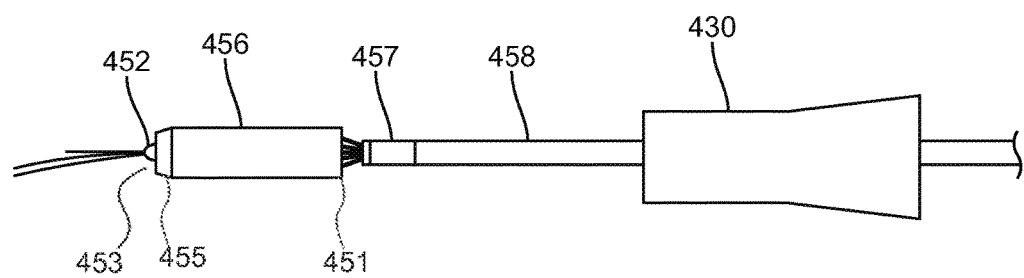

As shown in FIG. 35, while in funnel 430, a portion of prosthetic valve 460 can be arranged about landing zone 457. Prosthetic valve 460 can be attached to delivery system in a similar fashion as described above in reference to FIGS. 28-30 and then outer sheath 458 can be advanced to cover landing zone 457 and a portion of prosthetic valve 460. After prosthetic valve 460 is attached, prosthetic valve 460 can be pulled within retaining tube 456 as illustrated in FIGS. 36 and 37. Then, as illustrated in FIG. 38, funnel 430 can be removed leaving prosthetic valve 460 within retaining tube 456. Retaining tube 456 can have a funnel-like shape defined by a proximal end 451 having a first diameter and a distal end 453 having a second diameter. Proximal end 451 and distal end 453 may be separated by a tapered region 455 with the first diameter being larger than the second diameter. Preferably, the first diameter of proximal end 451 is smaller than the first diameter at proximal end 431 of large funnel 430. Preferably, the first diameter of proximal end 451 is smaller than the second diameter of large funnel 430 at distal end 433, such that retaining tube 456 can slide through large funnel 430. As retaining tube 456 is passed over prosthetic valve 460 (or prosthetic valve is pulled through retaining tube 456) prosthetic valve may be further crimped. Then, outer sheath 458 can be slid over prosthetic valve 460 until outer sheath 458 reaches tip 452 of delivery device 450, encapsulating prosthetic valve 460 within outer sheath 458.

The system components described herein can be made from a variety of materials known in the art. These include, but are not limited to, stainless steel, nitinol, plastics, polymers, composites, and any other suitable material.

Figure 39:
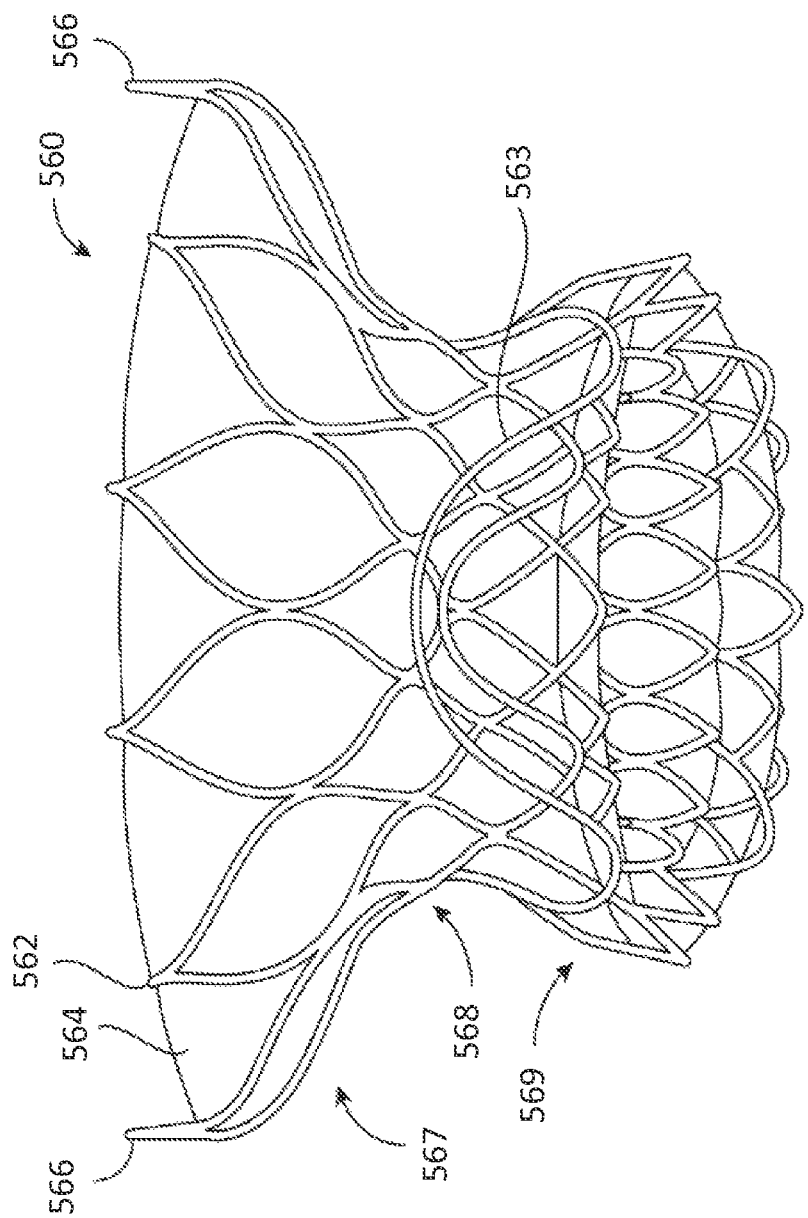
FIG. 39 illustrates a prosthetic heart valve, according to one embodiment.
Figure 40:
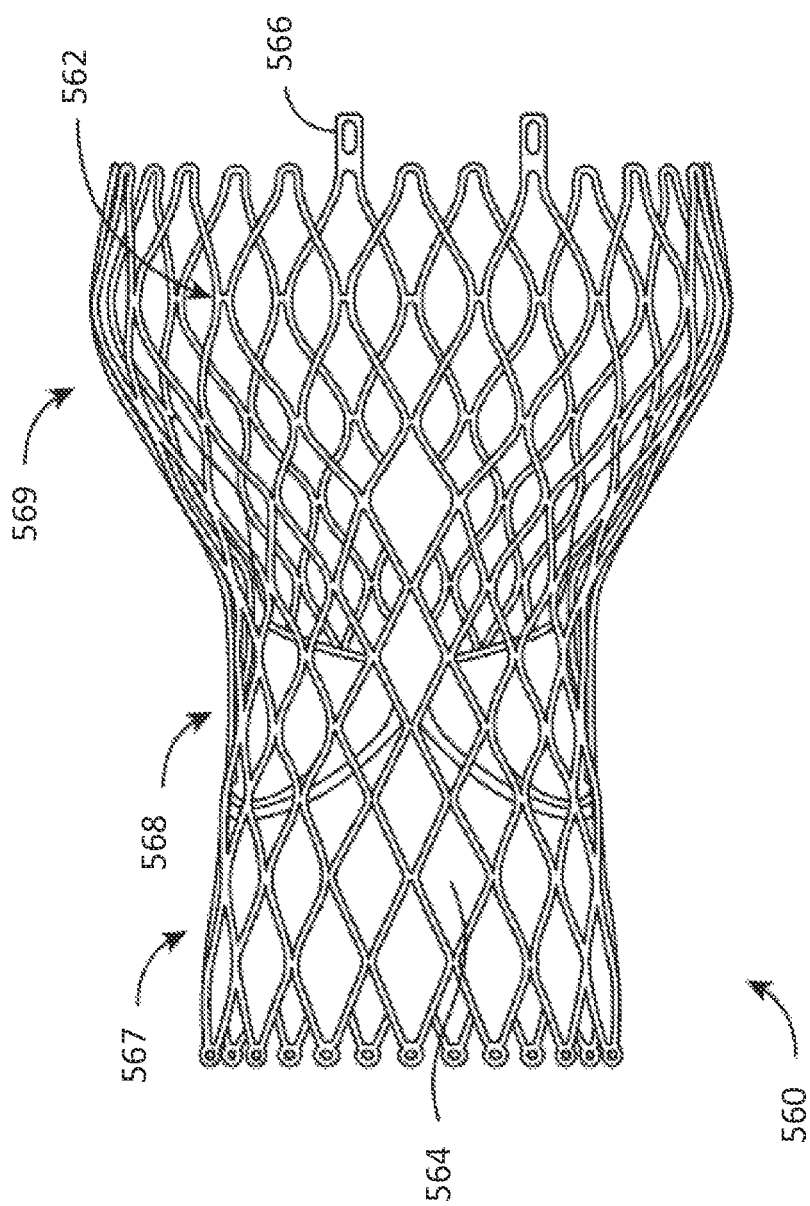
FIG. 40 illustrates a prosthetic heart valve, according to one embodiment.

Prosthetic valves as used in accordance with the devices and methods of the present disclosure can be generally used for replacement of a native aortic, mitral, pulmonic, or tricuspid valve, for use as a venous valve, or to replace a failed bioprosthesis. FIGS. 39 and 40 illustrate a prosthetic valve 560, according to one embodiment, that may be used in accordance with the devices and methods of the present disclosure. Prosthetic valve 560 can include a stent or stent frame 562 maintaining a valve structure (tissue or synthetic) 564. Frame 562 can include an inlet or inflow portion 567, a central portion 568, and an outlet or outflow portion 569. Frame 562 can include one or more tabs 566. Frame 562 can have an expanded arrangement for maintaining the prosthetic valve 560 in a desired implant location and a crimped, collapsed or compressed arrangement for loading within a delivery system. In certain embodiments, prosthetic valve 560 may or may not comprise one or more support arms 563.

The crimping systems according to various embodiments described herein provide for multi-component modular crimping systems with components that can be easily and reversibly connected via releasable attachment mechanisms. The releasably attached components provide for easily cleaning of the crimping system. Also, in the event that one of the components becomes damaged, that component can be easily replaced. The releasable and interchangeable nature of the components of the crimping systems described herein also allow for easy transport and reduce the space needed to perform a crimping operation. Additionally, the modular components of the crimping systems allow for a specific component to be interchanged with a component having an improved design and/or different size to accommodate future needs.

The foregoing description has been presented for purposes of illustration and description. It is not intended to be exhaustive or to limit the precise embodiments disclosed. Other modifications and variations may be possible in light of the above teachings. The embodiments and examples were chosen and described in order to best explain the principles of the embodiments and their practical application, and to thereby enable others skilled in the art to best utilize the various embodiments with modifications as are suited to the particular use contemplated. By applying knowledge within the skill of the art, others can readily modify and/or adapt for various applications such specific embodiments, without undue experimentation, without departing from the general concept. Therefore, such adaptations and modifications are intended to be within the meaning and range of equivalents of the disclosed embodiments, based on the teaching and guidance presented herein.

What is claimed is:

1. A system for crimping a prosthetic valve comprising:
   a first funnel, the first funnel comprising a first diameter of the first funnel, a tapered section, and a second diameter of the first funnel smaller than the first diameter of the first funnel;
   a second funnel, the second funnel comprising a first diameter of the second funnel, a tapered section, and a second diameter of the second funnel smaller than the first diameter of the second funnel;
   a delivery device, the delivery device comprising a strut support and an outer sheath, at least a portion of the delivery device extending through the first funnel and the second funnel wherein
      the second diameter of the first funnel and the second diameter of the second funnel face towards each other,
      the second diameter of the first funnel engages with the second diameter of the second funnel, and
      the first diameter of the first funnel and the first diameter of the second funnel face away from each other; and
   an actuator comprising a handle, a channel, a pull ring, and at least one wire operatively attached to the pull ring, an end of the at least one wire configured to attach to the prosthetic valve and pull the prosthetic valve through at least one of the first funnel and the second funnel through sliding of the pull ring;
   wherein the first diameter of the first funnel is larger than the first diameter of the second funnel.

2. The system of claim 1, wherein an outer diameter of the outer sheath is less than or equal to the second diameter of the first funnel and the second diameter of the second funnel.

3. The system of claim 1, wherein the first funnel and the second funnel are releasably connected.

4. The system of claim 1, wherein the actuator is configured to engage to the second funnel.

5. The system of claim 1, wherein the actuator is configured to engage to the first diameter of the second funnel.

6. The system of claim 1, wherein the first funnel is configured to directly connect to the second funnel, and the second diameter of the second funnel is configured to be fitted within the second diameter of the first funnel.

7. The system of claim 1, wherein the second diameter of the first funnel is configured to be fitted against the second diameter of the second funnel.

8. The system of claim 1, wherein the prosthetic valve is a self-expanding valve.

9. The system of claim 1, wherein the outer sheath is configured to slide over the strut support.

* * * * *